United States Patent
Yarranton et al.

(10) Patent No.: US 9,127,046 B2
(45) Date of Patent: *Sep. 8, 2015

(54) SECRETION OF ANTIBODIES WITHOUT SIGNAL PEPTIDES FROM BACTERIA

(75) Inventors: Geoffrey T. Yarranton, Burlingame, CA (US); Christopher R. Bebbington, San Mateo, CA (US)

(73) Assignee: KaloBios Pharmaceuticals, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/506,653

(22) Filed: May 7, 2012

(65) Prior Publication Data

US 2012/0309055 A1 Dec. 6, 2012

Related U.S. Application Data

(63) Continuation of application No. 11/273,906, filed on Nov. 14, 2005, now Pat. No. 8,211,648.

(60) Provisional application No. 60/701,902, filed on Jul. 22, 2005.

(51) Int. Cl.
| | | |
|---|---|---|
| C12N 15/00 | (2006.01) | |
| C12N 15/63 | (2006.01) | |
| C07K 16/00 | (2006.01) | |
| C07K 16/12 | (2006.01) | |

(52) U.S. Cl.
CPC .............. *C07K 16/00* (2013.01); *C07K 16/1214* (2013.01); *C07K 2317/21* (2013.01); *C07K 2317/55* (2013.01)

(58) Field of Classification Search
CPC ....... C12N 15/00; C12N 15/63; C12N 5/0601
USPC .......... 435/7.1, 252.33, 488, 69.1; 506/18, 26, 506/388.1; 536/25.53
See application file for complete search history.

(56) References Cited

U.S. PATENT DOCUMENTS

| | | | |
|---|---|---|---|
| 5,223,409 A | | 6/1993 | Ladner et al. |
| 5,576,184 A | | 11/1996 | Better et al. |
| 5,629,172 A | | 5/1997 | Mascarenhas et al. |
| 5,733,743 A | | 3/1998 | Johnson et al. |
| 5,824,502 A | | 10/1998 | Honjo et al. |
| 5,843,685 A | * | 12/1998 | Better et al. ................. 435/7.23 |
| 5,914,254 A | | 6/1999 | Mascarenhas et al. |
| 6,204,023 B1 | | 3/2001 | Robinson et al. |
| 6,331,415 B1 | | 12/2001 | Cabilly et al. |
| 7,288,249 B2 | | 10/2007 | Carter et al. |
| 8,211,648 B2 | * | 7/2012 | Yarranton et al. ............. 435/7.1 |
| 2005/0255552 A1 | | 11/2005 | Flynn et al. |

FOREIGN PATENT DOCUMENTS

| | | |
|---|---|---|
| EP | 0722461 | 10/2004 |
| JP | 03-280884 | 12/1991 |
| JP | 7-289267 | 11/1995 |
| JP | 09-313191 | 12/1997 |
| WO | WO 9002569 | 3/1990 |
| WO | WO 2004/094475 | 11/2004 |
| WO | WO 2004/108932 | 12/2004 |
| WO | WO 2005/019819 | 3/2005 |

OTHER PUBLICATIONS

U.S. Appl. No. 60/701,902, filed Jul. 22, 2005, Yarranton et al.
Derman, Alan et al., "A signal sequence is not required for protein export in prlA mutants of E. coli,"EMBO J., 1993, vol. 12, pp. 879-888.
Keyzer, Jeanine et al., "The F286Y mutation of prlA4 tempers the signal sequence suppressor phenotype by reducing the secA binding affinity,"FEBS Letters 2002, 510, pp. 17-21.
Perez-Perez, Julian et al., "Increasing the efficiency of protein export in E. coli,"Bio/Technology 1994, vol. 12, Feb. pp. 178-180.
Prinz, William et al., "Targeting of signal sequenceless proteins for export in E. coli with altered protein translocase,"EMBO J. 1996, vol. 15, pp. 5209-5217.
Mergulhao, F.J.M. et al., "Recombinant protein secretion in E. coli,"Biotechnol. Adv. May 2005, vol. 23, pp. 177-202.
Bost, Sandrine et al., "prl Mutations in the Escherichia coli secG gene," J. Biol. Chem. Feb. 1997, vol. 272, No. 7, pp. 4087-4093.
Khatib, Karim et al., "A novel class of secA alleles that exert a signal-sequence-dependent effect on protein export in E. coli," Genetics Nov. 2002, vol. 162, pp. 1031-1043.
Mallik, Ipsita et al., "Recognition of secretory proteins in E. coli requires signals in addition to the signal sequence and slow . . ." BMC Microbiology Nov. 2002,vol. 2, p. 32.
Smith, Margaret et al., "Modeling the effects of prl mutations on the E. coli secY complex,"J. Bacteriol., Sep. 2005, pp. 6454-6465.
Perez-Perez, Julian et al., "Different prlA proteins increase the efficiency of periplasmic production of human interleukin-6 . . . ,"J. Biotechnology 1996, vol. 49, pp. 245-247.
Liss, Laura et al., "Export defect adjacent to the processing site of Staphyococcal nuclease is suppressed by a prlA mutation," J. Bateriol. 1985, vol. 164, pp. 925-928.
Wong, Edith, "Expression of secreted insulin-like growth factor-1 in E. coli," Gene 1988, vol. 68, pp. 193-203.
Adams, Hendrik et al., "Defective translocation of a signal sequence mutant in a prlA4 suppressor strain . . . ," Eur. J. Biochemistry 2002, vol. 269, pp. 5572-5580.
Andersen, Christian et al., "Chunnel vision: export and efflux through bacterial channel-tunnels,"EMBO Reports 2000, vol. 1, pp. 313-318.
Bessonneau, Pascal et al., "The secYEG preprotein translocation channel is a conformationally dynamic and dimeric structure,"EMBO J. 2002, vol. 21, pp. 995-1003.
Boss, Michael et al., "Assembly of functional antibodies from immunoglobulin heavy and light chain synthesized . . . ,"Nucl. Acids Res. 1984, vol. 12, pp. 3791-3806.

(Continued)

*Primary Examiner* — Lynn Bristol
(74) *Attorney, Agent, or Firm* — HelixIP LLP

(57) ABSTRACT

The present invention is directed generally to compositions and methods for obtaining secretion of antibodies or antigen-binding antibody fragments from prokaryotes without the need for a signal peptide through making use of mutant host strains with altered secretory properties. In particular, the invention provides host cells and methods for obtaining secretion of antibodies or antigen-binding antibody fragments from bacteria without the need for a signal peptide and provides diverse libraries of antibody sequence resulting from such methods. The invention additionally provides diverse libraries.

7 Claims, 7 Drawing Sheets

(56) References Cited

OTHER PUBLICATIONS

Bothman, Hendrick et al., "The periplasmic E. coli peptidylprolyl . . . ,"J. Biol. Chem. Jun. 2000, vol. 275, pp. 17100-17105.
Bothman, Hendrick et al., "Selection for a periplasmic factor improving phage display and functional periplasmic . . . ,"Nature Biotechnol. Apr. 1998, vol. 16, pp. 376-380.
Bowden, Gregory et al., "Abnormal fractionation of beta-lactamase in E. coli: evidence for . . . ,"J. Bacteriol. May 1992, vol. 174, pp. 3407-3410.
Cabilly, Shmuel et al., "Generation of antibody activity from immunoglobulin polypeptide chains produced in . . . ,"Proc. Natl Acad. Sci. Jun. 1984, vol. 81, pp. 3273-3277.
Emr, Scott et al., "Localization and processing of outer membrane and periplasmic proteins . . . ,"J. Biol. Chem., May 1982, vol. 257, pp. 5852-5860.
Fekkes, Peter et al., "Protein targeting to the bacterial cytoplasmic membrane,"Microbiol. Molc. Biol. Rev., Mar. 1999, vol. 63, pp. 161-173.
Fernandez, Luis et al., "Formation of disulphide bonds during secretion of proteins . . . ,"Molc. Microbiol. 2001, vol. 40, pp. 332-346.
Field, Helen et al., "Expression of mouse immunoglobulin light and heavy chain variable regions . . . ,"Protein Engineer. 1989, vol. 3, pp. 641-647.
Flower, Ann et al., "prlA and prlG suppressors reduce the requirement for signal sequence recogniation,"J. Bacteriol. Sep. 1994, vol. 176, pp. 5607-5614.
Francetic, Olivera et al., "prlA suppression of defective export of maltose-binding protein in secB mutants of E. coli,"J. Bacteriol., Jul. 1993, pp. 4036-4044.
Gao, Changshou et al., "A method for the generation of combinatorial antibody libraries using pIX phage display,"Proc. Natl Acad. Sci. Oct. 2002, vol. 99, pp. 12612-12616.
Gentschev, Ivaylo et al., "The E. coli alpha-hemolysin secretion system and its use in vaccine development," Trends Microbiol. Jan. 2002, vol. 10, pp. 39-45.
King, David et al., "Expression, purification and characterization of B72.3 Fv fragments," Biochemistry J. 1993, vol. 290, pp. 723-729.
Mallik, Ipsita et al., "Recognition of secretory proteins in E. coli requires signals . . . ," BMC Microbiol. Nov. 2002, vol. 2, pp. 1-6.
Martineau, Pierre et al., "Expression of antibody fragment at high levels in the bacterial cytoplasm," J. Molc. Biol. 1998, vol. 280, pp. 117-127.
Peters, Elizabeth et al., "Membrane insertion defects caused by positive charges in the early mature region . . . ," J. Bacteriol. Jul. 1994, vol. 176, pp. 4296-4305.
Pluckthun, Andreas, "Biotechnological aspects of antibody production in E. coli," Acta Biotechnol. 1991, vol. 11, pp. 449-456.
Pluckthun, Andreas, Strategies for expression of antibody fragments in E. coli Methods: A Companion to Methods in Enzymology Apr. 1991, vol. 2, pp. 88-96.
P.W. Van Der Wolk, Jeroen et al., "PrlA4 prevents the rejection of signal sequence defective preproteins by stabilizing . . . ," EMBO J. 1998, vol. 17, pp. 3631-3639.
Rockenbach, Sue et al., "Secretion of active truncated CD4 into E. coli periplasm," Appl. Microbiol. Biotechnol. 1991, vol. 35, pp. 32-37.
Sako, Tomoyuki, "Novel prlA alleles defective in supporting Staphylokinase processing in E. coli," J. Bacteriol., Apr. 1991, pp. 2289-2296.
Skerra, Arne et al., "Secretion and in vivo folding of the Fab fragment of the antibody McPC603 in E. coli . . . ," Protein Engineer. 1991, vol. 4, pp. 971-979.
Triplett, Terry et al., "Functional signal peptides bind a soluble N-temrinal fragment of . . . ," J. Biol. Chem., Jun. 2001, vol. 276, pp. 19648-19655.
Ulrich, Helle et al., "Expression studies of catalytic antibodies," Proc. Natl Acad. Sci., Dec. 1995 vol. 92, pp. 11907-11911.
Venturi, Miro et al., "High level producion of functional antibody Fab fragments in an oxidizing bacterial cytoplasm . . . ," J. Molc. Biol. 1992, vol. 315, pp. 1-8.
PCT International Search Report dated Jul. 7, 2008.
Supplementary European Search Report dated Oct. 21, 2009, Eur. Pat. Appln No. 06786474.4-2405.
Australian Examination Report, Oct. 23, 2009, Aust. Pat. Appln 2006276823.
Response to Australian Examination Report, Feb. 19, 2010, Aust. Pat. Appln 2006276823.
Australian Notice of Acceptance, Apr. 12, 2010, Aust. pat. Appln 2006276823.
Canadian Office Action, May 27, 2010, Can. Appln No. 2,615,776.
Response to Canadian Office Action, Nov. 25, 2010, Can. Appln No. 2,615,776.
EPO Office Action, Dec. 11, 2009, Eur. Pat. Appln No. 06786474.4-2405.
EPO Office Communication, Mar. 9, 2010, Eur. Pat. Appln No. 06786474.4-2405.
Response to EPO Office Action and Office Communication, Jul. 6, 2010, Eur. Pat. Appln No. 06786474.4-2405.
EPO Office Action, Jul. 27, 2010, Eur. Pat. Appln No. 06786474.4-2405.
Response to EPO Office Action, Nov. 2, 2010, Eur. Pat. Appln No. 06786474.4-2405.
New Zealand Examination Report, Dec. 21, 2009, NZ Pat. Appln No. 565126.
Response to NZ Examination Report, Mar. 11, 2010, NZ Pat. Appln No. 565126.
NZ Examination Report, Mar. 30, 2010, NZ Pat. Appln No. 565126.
Response to NZ Examination Report, May 14, 2010, NZ Pat. Appln No. 565126.
NZ Examination Report, Jun. 2, 2010, NZ Pat. Appln No. 565126.
Singaporean Search Report, Aug. 10, 2010, Appln No. 200800413-7.
Singaporean Written Opinion, Aug. 10. 2010, Appln No. 200800413-7.
EPO Office Action, May 19, 2011, Eur. Pat. Appln No. 06786474.4-2405.
Response to EPO Office Action, Oct. 18, 2011, Eur. Pat. Appln No. 06786474.4-2405.
EPO Office Action, Aug. 27, 2012, Eur. Pat. Appln No. 06786474.4-2405.
NZ Examination Report and Notice of Acceptance, Feb. 18, 2011, NZ Pat. Appln No. 565126.
Canadian Office Action, Feb. 13, 2012, Can. Pat. Appln No. 2,615,776.
Singapore Notification of Grant of Patent, Apr. 18, 2012, Appln No. 201109240-0.
Singapore Examination Report, Apr. 27, 2012, Appln No. 200800413-7.
Indian Examination Report, Jul. 18, 2011, Ind. Appln No. 518/DELNP/2008.
Response to Indian Examination Report, Feb. 1, 2012, Ind. Appln No. 518/DELNP/2008.
Response to ISR Office Action, Jan. 1, 2012, Israeli Patent Appln 188889.
Response to Canadian Office Action, Aug. 9, 2012, Can. Pat. Appln No. 2,615,776.
Haldl, Maryann et al., "N-terminal deletions of a mitochondrial signal sequence in yeast," J. Biol. Chem. 1989, vol. 264, pp. 17107-17112.
Kaytes, Paul et al., "High-level expression of human renin in Escherichia coli," J. Biotechnology, 1986, vol. 4, pp. 205-218.

* cited by examiner

```
  1 MAKQPGLDFQ SAKGGLGELK RRLLFVIGAL IVFRIGSFIP IPGIDAAVLA KLLEQQRGTI
 61 IEMFNMFSGG ALSRASIFAL GIMPYISASI IIQLLTVVHP TLAEIKKEGE SGRRKISQYT
121 RYGTLVLAIF QSIGIATGLP NMPGMQGLVI NPGFAFYFTA VVSLVTGTMF LMWLGEQITE
181 RGIGNGISII IFAGIVAGLP PAIAHTIEQA RQGDLHFLVL LLVAVLVEAV TFFVVFVERG
241 QRRIVVNYAK RQQGRRVYAA QSTHLPLKVN MAGVIPAIFA SSIIL YPATI ASWFGGGTGW
301 NWLTTISLYL QPGQPLYVLL YASAIIFFCF FYTALVFNPR ETADNLKKSG AFVPGIRPGE
361 QTAKYIDKVM TRLTLVGALY ITFICLIPEF MRDAMKVPFY FGGTSLLN VV VVIMDFMAQV
421 QTLMMSSQYE SALKKANLKG YGR
```

FIG. 1

SEQUENCE LISTING

```
<160> NUMBER OF SEQ ID NOS: 15

<210> SEQ ID NO 1
<211> LENGTH: 443
<212> TYPE: PRT
<213> ORGANISM: Escherichia coli

<400> SEQUENCE: 1

Met Ala Lys Gln Pro Gly Leu Asp Phe Gln Ser Ala Lys Gly Gly Leu
1               5                   10                  15

Gly Glu Leu Lys Arg Arg Leu Leu Phe Val Ile Gly Ala Leu Ile Val
            20                  25                  30

Phe Arg Ile Gly Ser Phe Ile Pro Ile Pro Gly Ile Asp Ala Ala Val
        35                  40                  45

Leu Ala Lys Leu Leu Glu Gln Gln Arg Gly Thr Ile Ile Glu Met Phe
    50                  55                  60

Asn Met Phe Ser Gly Gly Ala Leu Ser Arg Ala Ser Ile Phe Ala Leu
65                  70                  75                  80

Gly Ile Met Pro Tyr Ile Ser Ala Ser Ile Ile Ile Gln Leu Leu Thr
                85                  90                  95

Val Val His Pro Thr Leu Ala Glu Ile Lys Lys Glu Gly Glu Ser Gly
            100                 105                 110

Arg Arg Lys Ile Ser Gln Tyr Thr Arg Tyr Gly Thr Leu Val Leu Ala
        115                 120                 125
```

-continued

```
Ile Phe Gln Ser Ile Gly Ile Ala Thr Gly Leu Pro Asn Met Pro Gly
            130                 135                 140

Met Gln Gly Leu Val Ile Asn Pro Gly Phe Ala Phe Tyr Phe Thr Ala
145                 150                 155                 160

Val Val Ser Leu Val Thr Gly Thr Met Phe Leu Met Trp Leu Gly Glu
                165                 170                 175

Gln Ile Thr Glu Arg Gly Ile Gly Asn Gly Ile Ser Ile Ile Ile Phe
                180                 185                 190

Ala Gly Ile Val Ala Gly Leu Pro Pro Ala Ile Ala His Thr Ile Glu
                195                 200                 205

Gln Ala Arg Gln Gly Asp Leu His Phe Leu Val Leu Leu Leu Val Ala
            210                 215                 220

Val Leu Val Phe Ala Val Thr Phe Phe Val Val Phe Val Glu Arg Gly
225                 230                 235                 240

Gln Arg Arg Ile Val Val Asn Tyr Ala Lys Arg Gln Gln Gly Arg Arg
                245                 250                 255

Val Tyr Ala Ala Gln Ser Thr His Leu Pro Leu Lys Val Asn Met Ala
                260                 265                 270

Gly Val Ile Pro Ala Ile Phe Ala Ser Ser Ile Ile Leu Tyr Pro Ala
                275                 280                 285

Thr Ile Ala Ser Trp Phe Gly Gly Thr Gly Trp Asn Trp Leu Thr
            290                 295                 300

Thr Ile Ser Leu Tyr Leu Gln Pro Gly Gln Pro Leu Tyr Val Leu Leu
305                 310                 315                 320

Tyr Ala Ser Ala Ile Ile Phe Phe Cys Phe Phe Tyr Thr Ala Leu Val
                325                 330                 335

Phe Asn Pro Arg Glu Thr Ala Asp Asn Leu Lys Lys Ser Gly Ala Phe
            340                 345                 350

Val Pro Gly Ile Arg Pro Gly Glu Gln Thr Ala Lys Tyr Ile Asp Lys
                355                 360                 365

Val Met Thr Arg Leu Thr Leu Val Gly Ala Leu Tyr Ile Thr Phe Ile
370                 375                 380

Cys Leu Ile Pro Glu Phe Met Arg Asp Ala Met Lys Val Pro Phe Tyr
385                 390                 395                 400

Phe Gly Gly Thr Ser Leu Leu Asn Val Val Val Ile Met Asp Phe
                405                 410                 415

Met Ala Gln Val Gln Thr Leu Met Met Ser Ser Gln Tyr Glu Ser Ala
            420                 425                 430

Leu Lys Lys Ala Asn Leu Lys Gly Tyr Gly Arg
            435                 440

<210> SEQ ID NO 2
<211> LENGTH: 4
<212> TYPE: PRT
<213> ORGANISM: Artificial Sequence
<220> FEATURE:
<223> OTHER INFORMATION: chemically synthesized

<400> SEQUENCE: 2

Ile Pro Thr Gly
1

<210> SEQ ID NO 3
<211> LENGTH: 8
<212> TYPE: PRT
<213> ORGANISM: Artificial Sequence
```

```
<220> FEATURE:
<223> OTHER INFORMATION: chemically synthesized

<400> SEQUENCE: 3

Asp Tyr Lys Asp Asp Asp Asp Lys
1               5

<210> SEQ ID NO 4
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 4
ggaaacagta tacatggaca tccagttgac ccagtc                              36

<210> SEQ ID NO 5
<211> LENGTH: 90
<212> TYPE: DNA
<213> ORGANISM: Artificial Sequence
<220> FEATURE:
<223> OTHER INFORMATION: synthetic oligonucleotide

<400> SEQUENCE: 5
gccagtgaat tcaaacccct caagacccgt ttagaggccc caaggggtta tgctagttaa    60
tcgatttaac actctcccct gttgaagctc                                     90

<210> SEQ ID NO 6
<211> LENGTH: 4
<212> TYPE: DNA
<213> ORGANISM: Artificial Sequence
<220> FEATURE:
<223> OTHER INFORMATION: synthetic oligonucleotide

<400> SEQUENCE: 6 agga                                                                  4

<210> SEQ ID NO 7
<211> LENGTH: 7
<212> TYPE: PRT
<213> ORGANISM: Artificial Sequence
<220> FEATURE:
<223> OTHER INFORMATION: chemically synthesized

<400> SEQUENCE: 7

Met Asp Ile Gln Leu Thr Gln
1               5

<210> SEQ ID NO 8
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 8
ggaaacagta tacatggagg tgcagctggt ggagtc                              36

<210> SEQ ID NO 9
<211> LENGTH: 39
<212> TYPE: DNA
<213> ORGANISM: Artificial Sequence
<220> FEATURE:
<223> OTHER INFORMATION: synthetic oligonucleotide
```

```
<400> SEQUENCE: 9
cacgatgcgg ccgcttaaca agatttgggc tcaactttc                              39

<210> SEQ ID NO 10
<211> LENGTH: 7
<212> TYPE: PRT
<213> ORGANISM: Artificial Sequence
<220> FEATURE:
<223> OTHER INFORMATION: chemically synthesized

<400> SEQUENCE: 10

Met Glu Val Gln Leu Val Glu
1               5

<210> SEQ ID NO 11
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 11
cgatgcgaat tcgactctag cgctgtggta tggctgtgca ggtcg                       45

<210> SEQ ID NO 12
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 12
tcttccaggc ctgagctcga gctgttgaca attaatca                               38

<210> SEQ ID NO 13
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 13
cagttacagg cctggtacct caccggccgt taaacccccc atggtttatt cc               52

<210> SEQ ID NO 14
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 14
acggaattca ccatggctaa acaaccggga ttagattttc                             40

<210> SEQ ID NO 15
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 15
cagttacggt accttatcgg ccgtagcctt tcaggttc                               38
```

SECRETION OF ANTIBODIES WITHOUT SIGNAL PEPTIDES FROM BACTERIA

CROSS-REFERENCES TO RELATED APPLICATION(S)

The present application claims the benefit of priority under 35 U.S.C. §119 from U.S. Provisional Patent Application Ser. No. 60/701,902 entitled "SECRETION OF ANTIBODIES WITHOUT SIGNAL PEPTIDES FROM BACTERIA", filed on Jul. 22, 2005, the disclosure of which is hereby incorporated by reference in its entirety for all purposes.

FIELD OF THE INVENTION

The present invention is directed generally to methods for secreting antibodies, antibody fragments, or antibody-related polypeptides from prokaryotes without the need for a signal peptide. In particular, the invention provides host cells and methods for secreting antibodies, antigen-binding antibody fragments, or antibody-related polypeptides from bacteria without the need for a signal peptide and provides diverse libraries of antibodies, antibody fragments, or antibody-related polypeptides resulting from such methods. The present invention is also directed at antibodies, antibody fragments, antibody-related polypeptides, and libraries of the same made by the methods of the invention.

BACKGROUND OF THE INVENTION

Most proteins destined for the periplasm or the outer membrane of gram negative bacteria, such as enteric bacteria, are transported across the cytoplasmic membrane by the general secretory pathway or Sec system, a complex of proteins, which identifies polypeptides for export and translocates them across the cytoplasmic membrane. This system has been used to secrete mammalian proteins from the enteric bacteria *E. coli*, including antibody fragments. Natural prokaryotic secreted proteins and heterologous proteins such as mammalian proteins are directed to the secretory apparatus by the addition of a functional signal peptide, a sequence of typically between 13 and 30 amino acids at the N-terminus of the protein which has a hydrophobic core and additional sequences to direct the nascent polypeptide chain to the secretory apparatus and allow accurate removal of the signal peptide after secretion. A number of prokaryotic signal peptides have been described which allow efficient secretion of at least some antibody fragments, including the signal peptides from the *Erwinia caratovora* pectate lyase B (PelB) protein, *Escherichia coli* heat-stable enterotoxin (StII) and the *E. coli* OmpA protein. Other prokaryotes have similar secretory systems, and signal peptides have been described for many for these other prokaryotes.

However, secretion systems are highly variable in the efficiency with which antibodies, antibody fragments or antibody-related polypeptides are secreted. The efficiency of secretion is dependent on the sequence of the variable regions of both the heavy and the light chains of antibodies. For example, Fab fragments containing murine V-regions are poorly secreted if at all. Further, human Fab fragments are secreted with variable efficiency, depending on the V-region sequence, and/or $V_H$ subclass. Such variable secretion efficiency leads to bias in the sequences of antibodies which may be screened from a generated antibody library.

In some cases, mutations in the V-region can be introduced in order to improve secretion. However, alterations in the amino acid sequence of antibody V-regions may compromise antibody function and are not generally desirable.

Furthermore, cleavage of signal peptides from the secreted polypeptide is not always efficient. For example, the signal peptide of *E. coli* OmpA or PhoA is not cleaved from a fusion protein with human interleukin-1 beta (IL-1 beta) when the fusion protein is expressed in *E. coli*.

It is an object of the present invention to provide compositions and methods for obtaining secretion of antibodies, antibody fragments, or antibody-related polypeptides from bacteria without the need for a signal sequence thereby removing any secretion constraints caused by variable region sequence.

SUMMARY OF THE INVENTION

The present invention relates to methods for secreting antibodies, antibody fragments, and/or antibody-related polypeptides in prokaryotes without the need for a signal peptide thereby overcoming limitations imposed by variable region sequences In one embodiment, the methods of the invention comprise expressing polynucleotides encoding antibodies, antibody fragments, or antibody-related polypeptides without a signal sequence in a prokaryotic host cell, followed by secretion of the antibodies, antibody fragments, or antibody-related polypeptides across the cytoplasmic membrane of the host cell. In an embodiment of the invention, antibodies, antibody fragments, or antibody-related polypeptides are secreted without a signal sequence by use of a prokaryotic host cell that contains one or more mutations in the gene(s) which encode the proteins of the cells secretory pathway(s). In another embodiment, the host cell is *E. coli* and the secretory mutant is a Protein-localization (prl) mutant.

The present invention also relates to libraries of antibodies or related polypeptides that are made by the methods of the invention. In one embodiment, the libraries of the invention comprise antibody, antibody fragment, or antibody-related polypeptide clones that cannot be secreted or are difficult to secrete in prokaryotes when signal sequences are used to direct transport across the cytoplasmic membrane. In another embodiment, the antibody, antibody fragment, antibody-related polypeptide, or other polypeptide libraries of the invention have better representation of different VH and VL subclasses than libraries expressed with signal sequences. The antibodies and related polypeptides of the invention include intact immunoglobulins, single chain antibodies, Fab, Fab', F(ab')2, Fv, camelid antibodies, antigen-binding scaffolds, antibody or antibody-related polypeptide fusion proteins, and other polypeptides disclosed below.

In another embodiment, the antibody-related polypeptides of the invention include antigens that are recognized by the antibodies, antibody fragments, or antibody-related polypeptides of the invention. In an embodiment of the invention, these antigens are self-antigens.

In an embodiment of the invention, the methods of the invention allow for expression, secretion, and assembly of multimeric proteins wherein one or more subunit of the multimeric protein lacks a functional signal sequence.

BRIEF DESCRIPTION OF THE FIGURES

For a better understanding of the nature and objects of some embodiments of the invention, reference should be made to the following detailed description taken in conjunction with the accompanying drawings, in which:

FIG. 1 is a diagram showing the amino acid sequence of *E. coli* Sec Y protein from mutant F286Y and I408N (prlA4), where the mutated amino acids are shown underlined in bold (SEQ ID NO:1).

DETAILED DESCRIPTION OF THE INVENTION

Definitions

Figure 2:
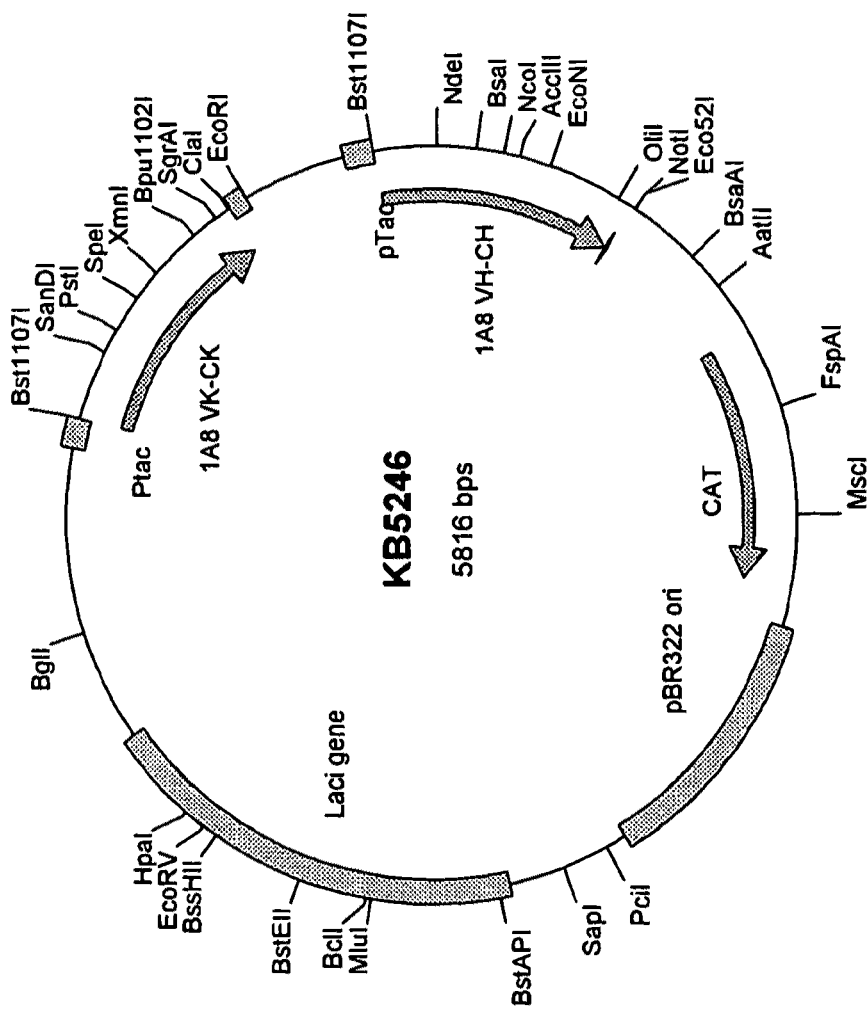
FIG. 2 shows a plasmid map of a vector used for expression of heavy and light chain genes for an antibody fragment without a signal peptide in *E. coli*. The plasmid has a chloramphenicol-acetyl transferase gene to confer resistance to chloramphenicol and a lacIq gene which expresses a lac repressor for regulation of gene expression. The light and heavy chain genes are each under the control of a tac promoter and expression is inducible by lactose or IPTG.

As used herein, "antigen" refers to substances that are capable, under appropriate conditions, of reacting with specific antibodies, antibody fragments, or antibody-related polypeptides. Antigens can be soluble substances, such as toxins or foreign proteins, however, only the portion of the protein or antigenic molecule known as the antigenic determinant (epitope) combines with the antibody, antibody fragment, or antibody-related polypeptide. More broadly, the term "antigen" is used herein to refer to any substance to which an antibody binds, or for which antibodies are desired, regardless of whether the substance is immunogenic. For such antigens, antibodies can be identified by recombinant methods, independently of any immune response.

As used herein, an "antibody" refers to a protein functionally defined as a binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical antibody structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region (V) of about 100 to 110 or more amino acids primarily responsible for antigen recognition. The terms variable light chain (VL) and variable heavy chain (VH) refer to these light and heavy chains respectively.

Antibodies exist as intact immunoglobulins, as a number of well characterized fragments produced by digestion with various peptidases, or as a variety of fragments made by recombinant DNA technology. Thus, for example, papain digests antibodies into an antigen binding Fab fragment and a residual Fc fragment; pepsin digests an antibody below the disulfide linkages in the hinge region to produce F(ab')$_2$, a dimer of Fab which itself is a light chain joined to VH-CH1 by a disulfide bond. The F(ab')$_2$ may be reduced under mild conditions to break the disulfide linkage in the hinge region thereby converting the F(ab')$_2$ dimer into an Fab' monomer. The Fab' monomer is essentially a Fab with part of the hinge region (see, W. E. Paul, ed., 1993, *Fundamental Immunology*, Raven Press, NY, for a more detailed description of other antibody fragments). While various antibody fragments are defined in terms of the digestion of an intact antibody, one of skill in the art will appreciate that such Fab' fragments or other fragments may be synthesized de novo either chemically or by utilizing recombinant DNA methodology. In addition, recombinant DNA methodologies may be used to create antibody fragments that cannot be made by enzymatic digestion. Thus, the term antibody, as used herein also includes antibody fragments either produced by the modification of whole antibodies or synthesized de novo using recombinant DNA methodologies. Antibodies include single chain antibodies (antibodies that exist as a single polypeptide chain), including single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker (Huston, et al., 1988, *Proc. Nat. Acad. Sci. USA*, 85: 5879-5883). While the VH and VL are connected to each other as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743, which is incorporated herein by reference in its entirety). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies include all those that have been displayed on phage (e.g., scFv, Fv, Fab and disulfide linked Fv (Reiter et al., 1995, Protein Eng. 8: 1323-1331). Antibodies can also include diantibodies and miniantibodies.

Antibodies can derive from multiple species. For example, antibodies include rodent (such as mouse and rat), rabbit, sheep, camel, and human antibodies. Antibodies can also include chimeric antibodies, which join variable regions from one species to constant regions from another species. Likewise, antibodies can be humanized, that is constructed by recombinant DNA technology to produce immunoglobulins which have human framework regions from one species combined with complementarity determining regions (CDR's) from a another species' immunoglobulin (see, e.g., EPO Publication No. 0239400). In the case of antibodies, the modules consist of "framework" and "CDR" modules. By creating separate framework and CDR modules, different combinatorial assembly possibilities are enabled. Moreover, if two or more artificial genes carry identical pairs of cleavage sites at the boundaries of each of the genetic sub-elements, pre-built libraries of sub-elements can be inserted in these genes simultaneously, without any additional information related to any particular gene sequence. This strategy enables rapid optimization of, for example, antibody affinity, since DNA cassettes encoding libraries of genetic sub-elements can be (i), pre-built, stored and reused and (ii), inserted in any of these sequences at the right position without knowing the actual sequence or having to determine the sequence of the individual library member. Exemplary methods for generating synthetic libraries of antibodies are disclosed in, for example, U.S. Pat. Nos. 5,885,793 and 6,300,064, which are incorporated herein by reference in their entirety.

Antibodies also include epitope-focused antibodies, which have at least one minimal essential binding specificity determinant from a heavy chain or light chain CDR3 from a reference antibody, methods for making such epitope-focused antibodies are described in U.S. patent application Ser. No. 11/040,159, which is incorporated herein by reference in its entirety.

The term "cytoplasmic membrane" refers to a membrane that encloses the cytoplasm of a cell and, in a bacterium, lies internal to the periplasm and outer membrane in gram negative bacteria.

As used herein, the term "diversity" refers to the number of different specific antigen binding antibodies or related polypeptides.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

As used herein, the term "framework region" refers to those portions of immunoglobulin light and heavy chain variable regions that are relatively conserved (i.e., other than the CDRs) among different immunoglobulins in a single species, as defined by Kabat. As used herein, a "human framework region" is a framework region that is substantially identical (about 85% or more) to the framework region of a naturally occurring human antibody.

As used herein, the term "fusion antibody" refers to a molecule in which an antibody is fused to a non-antibody polypeptide at the N- or C-terminus of the antibody polypeptide. In one embodiment the antibody fragment may comprise one or more C-terminal peptide tags to facilitate detection and purification. In another embodiment the antibody may be fused to a peptide or polypeptide for display on the surface of a cell, spore or virus. For example one chain of the antibody fragment may be displayed as a fusion protein on the surface of a bacteriophage such as a filamentous phage.

The term "host cell" refers to a cell that provides the cellular machinery for expression and secretion of a polypeptide from an expression vector.

The term "humanized antibody" refers to antibodies constructed by recombinant DNA technology to produce immunoglobulins which have human framework regions from one species combined with complementarity determining regions (CDR's) from another species' immunoglobulin (see, e.g., EPO Publication No. 0239400).

As used herein, the term "immunoglobulin" refers to tetrameric antibodies as well as a variety of forms besides antibodies; including, for example, Fv, Fab, and F(ab')$_2$ as well as bifunctional hybrid antibodies, fusion antibodies, chimeric antibodies, humanized antibodies, humaneered antibodies and single chain antibodies.

"Library" means a collection of nucleotides sequences, e.g., DNA, encoding antibodies or related polypeptides within clones; or a genetically diverse collection of antibodies or related polypeptides.

A "multimeric protein" as used herein refers to a globular protein containing more than one separate polypeptide or protein chain associated with each other to form a single globular protein in vitro or in vivo. The multimeric protein may consist of more than one polypeptide of the same kind to form a "homomultimer." Alternatively, the multimeric protein may also be composed of more than one polypeptide of distinct sequences to form a "heteromultimer." Thus, a "heteromultimer" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where more than two polypeptides are present. Exemplary structures for the heteromultimer include heterodimers (e.g. Fv and Fab fragments, diabodies, $GABA_B$ receptors 1 and 2 complexes), trimeric G-proteins, heterotetramers (e.g. F(ab')$_2$ fragments) and further oligomeric structures.

"Protein localization (prl) mutant" refers to a host cell with an alteration in its secretory apparatus which rescues the secretion-defect in proteins containing a defective signal peptide and in proteins without a signal peptide.

The terms "secretion/secrete/secreting" refers to transport from the cytoplasm of a cell across the cytoplasmic membrane, including transport pathways that require a signal sequence and transport pathways that do not require a signal.

The terms "signal sequence" and "signal peptide" both refer to a peptide sequence capable of aiding in the secretion of a connected nascent peptide to the outside of the host cell.

The terms "VH and VL subclasses" refer in humans to the 7 recognized VH sub-classes (VH1-VH7) and 16 VL sub-classes (Vkappa1-Vkappa6 and Vlambda1-Vlambda10).

The term "vector" includes any nucleic acid suitable for cloning or for expression of the nucleic acids of the invention in the host cells of the invention. The vector may, for example, be in the form of a plasmid, cosmid, viral particle, or phage. The vector may be self-regulating or may integrate into the host cell chromosome or other replication nucleic acid in the host cell. The vector may also be non-replicating or may poorly replicate, for example, in a transient expression system.

Expression Systems of the Invention

The invention provides methods for secretion of antibodies, antibody fragments, or antibody-related polypeptides from prokaryotic host cells without the need for a signal peptide. In one aspect of the invention there is provided a new method for secretion of an antibody or an antigen-binding fragment and its assembly into a functional antigen binding molecule. The antibody is encoded by one or more nucleic acids that comprise the coding sequences for the V region for an antibody. Antibodies of the invention may contain signal sequences, as described in U.S. Pat. No. 6,204,023, which is incorporated herein by reference in its entirety. In some embodiments, the antibodies or multimeric proteins of the invention are expressed from one or more polynucleotides encoding polypeptides lacking a signal peptide. The antibody is encoded by one or more vector(s) capable of expressing an antibody, antibody fragment, or antibody-related polypeptide. If the antibody is formed from a heavy and a light chain, coding sequences for both chains may be present on the same vector or the coding sequences may be present on different vectors within the transformed host cell. In a preferred embodiment, either the heavy or light chain of an antibody is expressed from a polynucleotide which does not encode a signal sequence. In some preferred embodiments, both heavy and light chains are encoded by polynucleotides which do not encode signal sequences. Embodiments of vectors include plasmids, viral vectors, episomes and chromosomal integrants.

Generally, recombinant expression vectors will include at least one origin of replication, phenotypic selectable markers permitting selection in host cells, e.g., the ampicillin resistance gene of *E. coli* and *Saccharomyces cerevisiae* TRP1 gene, a functional promoter to direct transcription of a downstream structural sequence, as well as suitable translation initiation and termination signals in operable reading frame. Suitable prokaryotic hosts for transformation include species in the family Enterobacteriaceae such as *E. coli*, or *Salmonella typhimurium*, various species within the genera *Pseudomonas, Streptomyces*, and *Staphylococcus*, other species such as *Bacillus subtilis*, and other bacterial hosts may also be employed as a matter of choice.

There are many expression systems for producing the polypeptides of the invention that are well known to those of ordinary skill in the art. (See, e.g., Fernandes and Hoeffler, Eds., 1999, *Gene Expression Systems*, Academic Press.) Large numbers of suitable vectors are known to those of skill in the art and are commercially available for generating the recombinant constructs of the present invention. The following vectors are provided as a representative but nonlimiting example: bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia), pSKF, pET23D, λ-phage derived vectors, p15A-based vectors (Rose, 1988, *Nucleic Acids Res.* 16:355 and 356) and fusion expression systems such as GST and LacZ. Some expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed.

Typically, the expression of the polynucleotide that encodes the polypeptide is under the control of a promoter that is functional in the desired host cell. A wide variety of promoters is available, and can be used in the expression vectors of the invention. Ordinarily, the selection of the promoter depends upon the cell type in which the promoter is to be used. Such promoters can be derived from operons encoding glycolytic enzymes such as acid phosphatase, or heat shock proteins, among others. Particular named bacterial promoters include lacI, lacZ, T3, T7, gpt, lambda $P_R$, tac and trc. Commonly used prokaryotic promoters include the beta-lactamase (penicillinase) and lactose (lac) promoter systems (Change, et al., 1990, *Nature* 198: 1056), the tryptophan (trp) promoter system (Goeddel et al., 1980, *Nucleic Acids Res.* 8: 4057), the tac promoter (DeBoer, et al, 1983, *Proc. Natl. Acad. Sci. U.S.A.* 80:21-25); and the lambda-derived $P_L$ promoter and N-gene ribosome binding site (Shimatake et al., 1981, *Nature* 292: 128). The particular promoter system is not critical to the invention, any available promoter that functions in prokaryotes can be used. Selection of the appropriate vector and promoter is well within the level of ordinary skill in the art.

For expression of polypeptides in prokaryotic cells other than *E. coli*, regulatory sequences for transcription and translation that function in the particular prokaryotic species are required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Sambrook et al., *Molecular Cloning A Laboratory Manual*, Cold Spring Harbor Laboratory, N.Y. and Ausubel et al., *Current Protocols in Molecular Biology*, Greene Publishing Associates and Wiley Interscience, N.Y. Bacterial expression systems for expressing the proteins of the invention are available in, e.g., *E. coli*, *Bacillus* sp., and *Salmonella* (Palva et al., 1983, *Gene* 22:229-235; Mosbach et al., 1983, *Nature* 302:543-545). Kits for such expression systems are commercially available.

Either constitutive or regulated promoters can be used in the present invention. Methods for regulating expression in *E. coli* are well known in the art and include the use of inducible promoters such as the lac or lac promoters which are inducible by IPTG, and arabinose-inducible promoters. Regulated promoters can be advantageous because the concentration of heterologous protein in the host cell can be controlled. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al., 1983, *Gene* 25: 167; de Boer et al., 1983, *Proc. Nat'l. Acad. Sci. USA* 80: 21), and the bacteriophage T7 promoter (Studier et al., 1986, *J. Mol. Biol.*; Tabor et al., 1985, *Proc. Nat'l. Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Other expression control sequences such as ribosome binding sites, transcription termination sites, operators, and the like may also be included. DNA constructs that include one or more of these control sequences are termed "expression cassettes." Accordingly, the nucleic acids that encode the polypeptides are incorporated for the desired level of expression in a desired host cell.

A translation-initiation codon may be introduced directly upstream of the mature antibody or antibody fragment coding sequence such that the antibody or antibody fragment polypeptide is expressed with a methionyl (or N-formyl methionyl) residue at the N-terminus. Additional sequences may be included in the coding sequence of the antibody, for example to facilitate purification or detection of the antibody or for another purpose. The heterologous structural sequence is assembled in the appropriate translational reading frame and with the appropriate translation initiation and termination sequences. Optionally, the heterologous sequence can encode a fusion protein including an N-terminal identification peptide imparting desired characteristics, e.g., stabilization or simplified purification of expressed recombinant product.

An ATG codon is present at the 5' end of the coding sequence such that the expressed protein has an N-formyl-methionine residue at the amino-terminus. Upon the expression of the coding sequence, the N-terminal amino acid may be retained or may be removed by proteases in the host cell. The antibodies, antibody fragments, or antibody-related polypeptides generated from expression of the DNA coding sequence according to this aspect of the invention are capable of binding antigen. In the event that the antibody fragment is formed from a heavy and a light chain, either or both chains may be expressed from a coding sequence with an ATG codon. Preferably both chains are expressed without a signal peptide.

Translational coupling may be used to enhance expression. The strategy uses a short upstream open translational reading frame derived from a highly expressed gene native to the translational system or a synthetical/non-natural highly expressed open reading frame, which is placed downstream of the promoter and ribosome binding site and upstream of a termination codon. Just prior to the termination codon is a second ribosome binding site, and following the termination codon is the initiation codon for the translation of the polypeptide to be expressed. The system allows for the efficient initiation of translation. See Squires, et. al., 1988, *J. Biol. Chem.* 263: 16297-16302.

Secreted antibodies can be detected in or isolated from the culture medium after a period of growth of the bacteria under conditions suitable for antibody expression. Methods for monitoring antibodies in the medium include Western blot analysis, SDS-PAGE and enzyme-linked immunosorption assays (ELISA). Secreted antibodies may also be detected in or isolated from the periplasm of the bacteria. Methods for disruption of the periplasm and release of antibody from the periplasmic fraction are well known in the art and include the use of low pH (eg pH4.0) or osmotic shock.

To facilitate purification of the polypeptides of the invention, the nucleic acids that encode the polypeptides can also include a coding sequence for an epitope or "tag" for which an affinity binding reagent is available. Such epitope tags include, e.g., c-myc, HA-tag, maltose binding protein, VSV-G tag, anti-DYKDDDDK (SEQ ID NO:3) tag, or any such tag, a large number of which are well known to those of skill in the art. Expression vectors useful for recombinant production of fusion polypeptides having these epitopes are commercially available (e.g., Invitrogen, Carlsbad, Calif.) vectors pcDNA3.1/Myc-His and pcDNA3.1N5-His are suitable for expression in mammalian cells). Additional expression vectors suitable for attaching a tag to the fusion proteins of the invention, and corresponding detection systems are known to those of skill in the art, and several are commercially available (e.g., "FLAG" (Kodak, Rochester N.Y.)). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E., 1990, "Purification of recombinant proteins with metal chelating adsorbents" in Genetic Engineering: Principles and Methods, J. K. Setlow, Ed., Plenum Press, NY; commercially available from Qiagen, Santa Clarita, Calif.).

One of skill would recognize that modifications can be made to the protein domains without diminishing their biological activity. Some modifications may be made to facilitate the cloning, expression, or incorporation of a domain into a polypeptide. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

Polypeptides

Antibodies

In one embodiment, the secreted polypeptides are antibodies. The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. The variable regions of each light/heavy chain pair form the antibody binding site. Thus, an intact antibody has two binding sites. Each chain has a constant region (C) and a variable region (V). Each chain is organized into a series of domains. The light chains have two domains, corresponding to the C region and the other to the V region. The heavy chains have four domains, one corresponding to the V region and three domains (1, 2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognizing the antigen and providing an antigen binding site. In even more detail, each V region is made up from three complementarity determining regions (CDR) separated by four framework regions (FR). The CDRs are the most variable part of the variable regions, and they perform the critical antigen binding function. The CDR regions are derived from many potential germ line sequences via a complex process involving recombination, mutation and selection.

Light chains are classified as either kappa or lambda. Heavy chains are classified as gamma, mu, alpha, delta, or epsilon, and define the antibody's isotype as IgG, IgM, IgA, IgD and IgE, respectively. Heavy chain subclasses in humans are designated VH1-VH7. Within light and heavy chains, the variable and constant regions are joined by a "J" region of about 12 or more amino acids, with the heavy chain also including a "D" region of about 10 more amino acids (see generally, 1993, Paul, W., ed., Fundamental Immunology, 3rd ed. Raven Press, N.Y., SH. 9 (incorporated by reference in its entirety for all purposes)).

From N-terminal to C-terminal, both light and heavy chain variable regions comprise alternating framework and complementarity determining regions (CDRs): FR, CDR. FR, CDR. FR, CDR and FR. The assignment of amino acids to each region is in accordance with the definitions of Kabat, 1987, and, 1991, supra, and/or Chothia & Lesk, 1987, *J. Mol. Biol.* 196: 901-917; Chothia et al., 1989, *Nature* 342: 878-883.

It has been shown that the function of binding antigens can be performed by fragments of a whole antibody. Exemplary binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment (Ward, E. S. et al., 1989, *Nature* 341: 544-546) which consists of a VH domain; (v) isolated CDR regions; and (vi) F(ab')$_2$ fragments, a bivalent fragment comprising two Fab fragments linked by a disulphide bridge at the hinge region.

In various embodiments of the invention, the antibody or antibody fragment may be a single-chain antibody or may be formed from a heavy and light chain. Examplary antibodies include intact immunoglobins, single chain antibodies, scFv, dAB, VHH, Fab, Fab', F(ab')2, Fv, camelid antibodies, nanobodies, antigen-binding scaffolds, and antibody or antibody-related polypeptide fusion proteins. If the antibody contains a heavy and a light chain, one or more chains is expressed without a signal peptide and preferably both chains are expressed without a signal peptide.

Two structures of IgGs constituting the immunoglobulins (antibody molecules) of camelids are known to exist: one a heterotetramer having heavy chains and light chains, and the other consisting of a heavy-chain dimer. The tetrameric structure is a common characteristic of IgGs among humans and most animals. On the other hand, the latter IgG having a heavy-chain dimer structure is considered characteristic of camelids.

Since the VH region of a heavy chain dimer IgG in a camelid does not have to make hydrophobic interactions with a light chain, the region in the heavy chain that normally contacts a light chain is changed to hydrophilic amino acid residues in a camelid. Due to structural differences compared to VHs of normal heterotetrameric IgGs, VH domains of the heavy-chain dimer IgGs are called Variable domain of the heavy-chain of heavy-chain antibody (VHH).

VHH has excellent solubility due to its hydrophilic amino acid residues. Amino acid substitutions are scattered throughout the primary structure (amino acid sequence) of VHH. Additionally, these hydrophilic amino acid residues form a cluster in the space of the tertiary structure of VH corresponding to the site that interacts with the VL domain. Herein, the aforementioned space of the tertiary structure is specifically called former VL side. These amino acid substitutions are, for example, V37F or V37Y, G44E, L45R or L45C, and W47 are also mostly substituted with Gly. Such substitutions increase the hydrophilicity of the former VL. side of VHH.

Furthermore, VHHs derived from camels and llamas have very high thermostability compared to mouse heterotetrameric antibodies. The use of VHH derived from these species can provide, for example, molecules that maintain their antigen binding ability even at 90° C. (Van der Linden et al., 1999, *Biochim. Biophys. Acta* 1431 (1): 37).

The diversity of antibody repertoire of camelids is determined by the complementary determining regions (CDR) 1, 2, and 3 in the VH or VHH regions. Possession of three CDRs is in common with the IgGs of other animal species. However, the CDR3 in the camel VHH region is characterized by its relatively long length averaging 16 amino acids (Muyldermans et al., 1994, *Protein Engineering* 7 (9): 1129). For example, compared to the CDR3 of mouse VH having an average of 9 amino acids, the CDR3 of camel IgG is very long.

Libraries of camelid-derived antibody variable regions, which maintain the in vivo diversity of the variable regions of a camelid, can be made by, for example, the methods disclosed in United States Patent Application Ser. No. 20050037421, published Feb. 17, 2005, which is incorporated herein by reference in its entirety.

In another embodiment of the invention, the antibody related polypeptides are scaffold polypeptides. Scaffold polypeptides are non-immunoglobulin binding polypeptides that exhibit selective binding activity toward a predetermined ligand. The non-immunoglobulin binding polypeptides are derived from an immunoglobulin-like domain containing scaffold that can be grafted with binding domains of a parent polypeptide to confer the binding specificity of the parent polypeptide onto the immunoglobulin-Like domain containing scaffold. The non-immunoglobulin binding polypeptides of the invention have the advantages of being stable and modular in both the scaffold domain structures as well as in the ability to accept a broad range of heterologous polypeptide binding domains. Additionally, the immunoglobulin-like domain containing scaffolds can be readily obtainable from human sources so that their immunogenecity when used as a human therapeutic is negligible. The scaffolds of the invention also can be readily constructed to contain or omit naturally occurring polysaccharide chains or to include novel chains or other extra-scaffold moieties or polypeptide structures.

In one embodiment, the invention is directed to non-immunoglobulin binding polypeptides having antibody variable region complementarity determining regions (CDRs) inserted into a Thy1 immunoglobulin-like domain containing scaffold. The CDRs are inserted into the loop regions of the Thy1 polypeptide which allows the CDRs to fold into a similar confirmation as they would be in the three dimensional structure of the donor, or parent, antibody. The resulting hybrid, or chimeric, antibody-related polypeptide exhibits similar binding characteristics compared to the parent antibody.

In another embodiment, the invention is directed to antibody-related polypeptides having altered immunoglobulin-like domain loops made by amino acid substitution at some or all positions. The altered amino acid sequences in the loop domains confer selective binding activity toward a ligand other than that bound by the antibody-related polypeptide. The amino acid alterations can be made at the nucleic acid or polypeptide level using a variety of methods known to those skilled in the art.

In yet another embodiment, the invention is directed to antibody-related polypeptides derived from the ThyOx family of immunoglobulin-like domain containing polypeptides. The ThyOx polypeptides can be used as an immunoglobulin-like domain containing scaffold or as a carrier polypeptide to generate an antibody-related polypeptide of the invention. Scaffold polypeptides and libraries of such Scaffold polypeptides may be made by methods including, for example, those disclosed in U.S. Patent Application No. 20040266993, published Dec. 30, 2004, which is incorporated herein by reference in its entirety.

As used herein, the term "immunoglobulin-like domain" or "Ig-like domain" when used in reference to a scaffold is intended to refer to an art-recognized β-sandwich structural motif found in proteins of diverse function, including for example, extracellular matrix proteins, muscle proteins, immune proteins, cell-surface receptors and enzymes. Ig-like domain members have been divided into various superfamilies, including for example, the immunoglobulin, fibronectin type III and cadherin superfamilies. Other superfamilies containing the Ig-like domain structural motif include, for example, members of the PKD domain, β-galactosidase/glucuronidase domain, transglutamase two C-terminal domains, actinoxanthin-like, CuZn superoxide dismutase-like, CBD9-like, lamin A/C globular tail domain, clathrin adaptor appendage domain, integrin domains, PapD-like, purple acid phosphatase N-terminal domain, superoxide reductase-like, thiol: disulfide interchange protein DsbD N-terminal domain and invasin/intimin cell adhesion fragments superfamilies. Ig-like domain structural similarity is maintained between members of different superfamilies irrespective of significant sequence identity. The term is intended to include Ig-like domain members within and across each superfamily. Therefore, the term "immunoglobulin-like (Ig-like) domain containing superfamily" is intended to refer to an Ig-like domain containing member polypeptide within any of these superfamilies as well as others known in the art. A description of the different Ig-like domain containing superfamilies can be found, for example, in Clarke et al., 1999, *Structure Fold. Des.* 7:1145-53 and within structural databases such as at the URL pdb.weizmann.ac.il/scop/da-ta/scop.b.c.b.html.

As used herein, the term "ThyOx" or "ThyOx family polypeptide" when used in reference to a antibody-related polypeptide of the invention is intended to mean a subclass of polypeptides within the immunoglobulin superfamily (IgSF) of immunoglobulin-like domain containing polypeptides that are related by their common β-sandwich structural motif and containing a scaffold framework structure similar to antibody variable region domains. Particular polypeptides within the ThyOx family of polypeptides include, for example, Thy-1, Ox2, GP40, Ox2-like protein and Ox2 homolog.

As used herein, the term "scaffold" is intended to mean a supporting polypeptide framework used to organize, orient and harbor heterologous binding domains or altered amino acid sequences conferring binding specificity to a ligand. A scaffold can be structurally separable from the amino acid sequences conferring binding specificity. The structurally separable portion of a scaffold can include a variety of different structural motifs including, for example, β-sandwich, β-sheet, α-helix, β-barrel, coil-coiled and other polypeptide secondary and tertiary structures well known in the art. A scaffold of the invention will also contain one or more regions that can be varied in amino acid sequence without substantially reducing the stability of the supporting framework structure. An exemplary region that can be varied includes a loop region segment that joins two strands of a β-sandwich or β-sheet. Amino acid residues corresponding to the structurally separated portion of a scaffold is referred to herein as a scaffold framework. Immunoglobulin-like domain containing scaffolds of the invention exhibit less than about 50% amino acid identity to a human immunoglobulin variable heavy or light chain framework amino acid sequence. Generally, immunoglobulin-like domain containing scaffolds will exhibit, for example, amino acid sequence identity less than about 45%, about 40%, about 30%, about 20%, about 15% or about 10% compared to a human immunoglobulin variable heavy or light chain framework amino acid sequence. Residues of a scaffold that can be varied are referred to herein with reference to its structural properties such as a loop region or with reference to its ability to accommodate altered residues. Therefore, a scaffold region that can be varied is referred to as a scaffold variable region, mutable region, exchange region, alterable region or changeable region, for example. Residues conferring secondary or tertiary structural properties can be retained, modified or conserved so long as the overall structure of the scaffold is maintained. Those skilled in the art know, or can determine, which residues function in structural stability of a polypeptide scaffold as well as the extent to which such residues can be modified.

Specific examples of scaffolds of the invention include immunoglobulin-like domain containing superfamily members. These superfamily members contain a immunoglobulin-like domain characterized as a β-sandwich which can be used as a scaffold of the invention. The β-sandwich consists of about 80-150 amino acid residues containing two layers of antiparallel β-sheet in which the flat hydrophobic faces of the β-sheets pack against each other. Each β-sheet contains a loop region that can be varied in amino acid sequence so as to confer unique binding specificity onto the scaffold polypeptide. Examples of Ig-like domain containing superfamily members include, for example, ThyOx family member polypeptides as well as the various individual members within the immunoglobulin-like domain containing superfamilies described previously. Such individual members include, for example, T cell receptor, CD8, CD4, CD2, class I MHC, class II MHC, CD1, cytokine receptor, GCSF receptor, GMCSF receptor, hormone receptors, growth hormone receptor, erythropoietin receptor, interferon receptor, interferon gamma receptor, prolactin receptor, NCAM, VCAM, ICAM, N-caderin, E-caderin, fibronectin, tenascin, and I-set containing domain polypeptides, or a functional fragment thereof. Exemplary descriptions of these an other Ig-like domain containing superfamily members can be found in, for example, Isacke and Horton, 2000, *The Adhesion Molecule FactsBook*, Second Ed., Academic Press, San Diego; Fitzgerald et al., 2001, *The Cytokine FactsBook*, Second Ed., Academic Press, San Diego; and Marsh et al., 1999, *The HLA FactsBook*, Second Ed., Academic Press, San Diego.

The antibodies, antibody fragments or antibody-related polypeptides of this invention may be derived from a variety of sources. In various embodiments, the antibodies, antibody fragments or antibody-related polypeptides are derived from mammalian genes and may be human, mouse, rabbit, sheep, rat, hamster chimeric, humanized, hybrid, or epitope-focused. The antibodies of this invention may be monoclonal. Owing to their high specificity for a given antigen, the advent of monoclonal antibodies (Kohler, G. and Milstein C, 1975, *Nature* 256: 495) represented a significant technical breakthrough with important consequences both scientifically and commercially.

Monoclonal antibodies are traditionally made by establishing an immortal mammalian cell line which is derived from a single immunoglobulin producing cell secreting one form of a biologically functional antibody molecule with a particular specificity. Because the antibody-secreting mammalian cell line is immortal, the characteristics of the antibody are reproducible from batch to batch. The key properties of monoclonal antibodies are their specificity for a particular antigen and the reproducibility with which they can be manufactured.

Early methods for producing monoclonals were laborious and time consuming. An animal of choice, e.g., a mouse, was immunized with a desired antigen, antibody producing cells were harvested from the animal (usually by splenectomy) and fused to a suitable immortalized cells, e.g., myeloma cells, to make a hybridoma that clonally produced an antibody. Such hybridoma technology is disclosed, for example, in U.S. Pat. Nos. 4,172,124 and 4,196,265; Zurawski et al, 1980, *Federation Proceedings* 39:4922; Frankel and Gerhard, 1979, *Molecular Immunology*, 16:101-106.

The introduction of transgenic animals that produce fully human antibodies has permitted the selection of hybridomas which also produce fully human antibodies. Such transgenic animals are disclosed, for example, in U.S. Pat. Nos. 6,075,181 and 6,300,129, which are incorporated herein by reference in their entirety.

Display technologies have also permitted the selection of monoclonal antibodies that are fully human or other animal, chimeric, synthetic, and/or semi-synthetic. One example of such display technologies is phage display (examples are disclosed in U.S. Pat. Nos. 5,565,332; 5,580,717; 5,821,047; 5,871,907; 5,885,793; 5,922,545; 5,403,484; 5,885,793; 6,172,197; 6,291,158; 6,291,650; and 6,387,627, which are incorporated herein by reference in their entirety) where a vectors for expression of fusion antibodies in which one or more antibody chain is fused at the N-terminus of a phage protein are constructed. Such vectors can be introduced into prl mutant host strains of the present invention in order to express antibodies and isolate phage-antibodies in a signal-independent manner. The expression of phage-antibodies in the host cells of the invention provides improved expression of poorly secreted antibodies and better representation of various sub-classes of antibodies present in libraries. The fusion proteins may also be expressed from polynucleotides encoding antibody fusion proteins lacking a signal sequence. Methods for screening, purifying and analyzing phage antibodies are described in the above patents. Another example of such display technologies is yeast display (examples are disclosed in U.S. Pat. No. 6,300,065, which is incorporated herein by reference in its entirety).

Phage-display technology has generally made use of the filamentous bacteriophage M13 or the closely related phage fd. These phages are composed of circular, single-stranded DNA surrounded by a cylinder of coat proteins. Most of the viral capsid consists of the major protein pVIII, of which there are approximately 2,700 copies per phage. At one end of the phage particle, there are five copies each of pIII and pVI that are involved in host-cell binding and in the termination of the assembly process. At the other end, there are five copies each of pVII and pIX, hydrophobic peptides of 33 and 32 amino acids, respectively, required for the initiation of assembly and for maintenance of virion stability.

Embodiments of the invention include chimeric antibodies and synthetic antibodies. The early monoclonal technologies described above produced non-human antibodies. These antibodies are potentially immunogenic in humans and this immunogenicity has severely hampered the development of therapeutic antibodies. The production of so called "chimeric antibodies," e.g., variable regions from one species joined to constant regions from another species, has been somewhat successful, but does not overcome the immunogenicity problem in many cases. Exemplary methods for chimerizing antibodies are disclosed in, for example, U.S. Pat. No. 4,816,567, which is incorporated herein by reference in its entirety.

Recombinant DNA technology has been utilized to produce immunoglobulins which have human framework regions from one species combined with complementarity determining regions (CDR's) from another species' immunoglobulin (see, e.g., EPO Publication No. 0239400). These new proteins are called "reshaped" or "humanized" (when the framework regions are human) immunoglobulins and the process by which the donor immunoglobulin is converted into a human-like immunoglobulin by combining its CDR's with a human framework is called "humanization". Exemplary methods for humanization of antibodies are disclosed in, for example, U.S. Pat. No. 6,180,370, which is incorporated herein by reference in its entirety.

Artificial antibodies and fragments thereof can be constructed based on known antibody sequences, which reflect the structural properties of a whole group of homologous antibody genes. Therefore it is possible to reduce the number of different genes without any loss in the structural repertoire. This approach leads to a limited set of artificial genes, which can be synthesized de novo, thereby allowing introduction of cleavage sites and removing unwanted cleavages sites. Furthermore, this approach enables (i), adapting the codon usage of the genes to that of highly expressed genes in any desired host cell and (ii), analyzing all possible pairs of antibody light (L) and heavy (H) chains in terms of interaction preference, antigen preference or recombinant expression titer, which is virtually impossible using the complete collection of antibody genes of an organism and all combinations thereof.

The use of a limited set of completely synthetic genes makes it possible to create cleavage sites at the boundaries of encoded structural sub-elements. Therefore, each gene is built up from modules which represent structural sub-elements on the protein/(poly)peptide level. In the case of antibodies, the modules consist of "framework" and "CDR" modules. By creating separate framework and CDR modules, different combinatorial assembly possibilities are enabled. Moreover, if two or more artificial genes carry identical pairs of cleavage sites at the boundaries of each of the genetic sub-elements, pre-built libraries of sub-elements can be inserted in these genes simultaneously, without any additional information related to any particular gene sequence. This strategy enables rapid optimization of, for example, antibody affinity, since DNA cassettes encoding libraries of genetic sub-elements can be (i), pre-built, stored and reused and (ii), inserted in any of these sequences at the right position without knowing the actual sequence or having to determine the sequence of the individual library member. Exemplary methods for generating synthetic libraries of antibodies are disclosed in, for example, U.S. Pat. Nos. 5,885,793 and 6,300,064, which are incorporated herein by reference in their entirety.

In one embodiment the antibodies are epitope-focused human antibodies created by methods for engineering antibodies where the resulting antibodies retain epitope binding specificity and affinity while at the same time having most of the non-human sequences replaced with human sequences, as described in patent application U.S. patent application Ser. No. 11/040,159, filed Jan. 20, 2005, which is incorporated herein by reference in its entirety. This is accomplished by transferring a BSD pair from the reference antibody, e.g., a protein of a CDR3 pair ($CDR3_2$). In antibodies that are affinity-matured, e.g., the reference antibody, the heavy chain and light chain BSDs are in close contact with one another and are optimized for mutual stabilization of the combined antigen-binding conformation, hence, they form a unit, i.e., a BSD pair. The antigen-binding conformation is, of course, dependent on the support of the underlying frameworks of the V-regions. When an affinity-matured BSD, e.g., that of the reference antibody, is combined with the structural diversity and stability of the complete human repertoire of heavy chain or light chain V-segment pairs, scaffolds that fully support the optimal antigen-binding conformation of the BSD are readily identified with the aid of selection systems including, but not limited to, phage display, cell viability, colony lift binding assays (CLBA), or a variety of immunoassays, e.g., ELISA assays.

Further, transfer of a BSD pair to diverse germline V-segments often result in selection of V-regions that that have affinities of greater than 50 nM. These selected V-regions can also be incorporated into the affinity maturation process of any antibody. V-segment libraries are relatively small without CDR3 repertoires, thus selection of human V-regions can also be combined with limited mutagenic diversification of one or both BSDs in libraries of searchable size for many conventional selection systems.

The V-segment repertoire used in generating libraries to replace the heavy and/or light chain V-segment of the reference antibody can be from any source. The human repertoires can be generated, e.g., by polymerase chain reaction (PCR) amplification using primers appropriate for the desired segments from cDNA obtained from peripheral blood or spleen, in which case the repertoires are expected to contain clones with somatic mutations. Alternatively, the repertoires can be obtained by amplification of genomic DNA from non-immune system cells in order to obtain germline-encoded sequences.

The human germline V-segment repertoire consists of 51 heavy chain V-regions, 40 κ light chain V-segments, and 31λ light chain V-segments, making a total of 3,621 germline V-region pairs. In addition, there are stable allelic variants for most of these V-segments, but the contribution of these variants to the structural diversity of the germline repertoire is limited. The sequences of all human germ-line V-segment genes are known and can be accessed in the V-base database, provided by the MRC Centre for Protein Engineering, Cambridge, United Kingdom (see, Chothia et al., 1992, *J Mol Biol* 227:776-798; Tomlinson et al., 1995, *EMBO J* 14:4628-4638; and Williams et al., 1996, *J Mol Biol* 264:220-232). V-segment variants generated by somatic hypermutagenesis during the affinity maturation process may also make important contributions to the V-segment repertoire, since these mutations appear to be non-random, and may confer structural adjustments which facilitate high-affinity antigen specificity. While naïve antibodies are optimized for broad specificity and low affinity for maximum binding diversity, affinity matured antibodies may contain structural adaptations which favor the more rigid CDRs required for high-affinity antigen-specific binding (e.g., Diaz and Klinman, 2000, *Immunol Res.* 21:89-102).

Human V-region repertoires, both germline and affinity-matured, can be recovered, e.g., from peripheral blood lymphocytes (PBL), often pooled from multiple (e.g., at least 10) healthy individuals, using conventional cDNA cloning methods (Sambrook and Russell, eds, *Molecular Cloning: A Laboratory Manual,* 3rd Ed, vols. 1-3, Cold Spring Harbor Laboratory Press, 2001). Insofar as the germline frequency distribution is not uniform in expressed sequences, it is prudent to capture at least $10^3$ independent clones for each of the three V-region isotypes (VH, Vκ, and Vλ) to ensure optimal diversity of the repertoires. The PCR can be used to amplify V-region sequences during the cloning process. However, exponential amplification mechanisms are prone to random biases, and this may be compounded by the use of degenerate primers, which have variable priming efficiencies, resulting in a loss of diversity. Thus, when amplification is desired, it may be desirable, where possible, to use a primer-independent linear amplification method, such as in vitro transcription (Sambrook and Russell, eds, *Molecular Cloning: A Laboratory Manual,* 3rd Ed, vols. 1-3, Cold Spring Harbor Laboratory Press, 2001).

BSDs from the reference antibody are transferred to a library of V-segment sequences generated as described above. The BSDs can be incorporated into the expression vector before or after the population of V-segments is cloned into the expression vector. The BSD that is transferred can be a CDR3-FR4, a CDR3, a D segment (where the BSD is from the heavy chain), a MEBSD, or any other fragment of CDR3-FR4 that has binding specificity in combination with the complementing BSD from the other chain of the reference antibody. It is understood that when transferring a BSD from a reference antibody to a different V-region, the structure of the heavy or light chain V region is maintained in the resulting V-region. Thus, if the BSD from the reference antibody is a subregion of CDR3-FR4, the complete CDR3-FR4 structural length is maintained, i.e., the remainder of the CDR3-FR4 residues that are not from the reference antibody are made up of other residues, typically human germline residues.

As noted, the BSD can include Framework 4 regions, e.g., from the reference antibody, which are part of the J-segments, but which are highly conserved among mammals, and are important for CDR3 structure. These sequences can, for example, be amplified by PCR with primers containing restriction sites for in-frame ligation to Framework 3, and other unique restriction sites downstream from the carboxyl terminus of Framework 4, e.g., for ligation to the C-region. Each CDR3-FR4 is then transferred into the appropriate sites of the V-region library construct. Alternatively, the desired sequence or mix of sequences for the CDR3-FR4 region can be synthesized as one continuous oligonucleotide or mix of oligonucleotides and can be joined to the V segment repertoire by primer extension using in vitro transcribed cRNA synthesized from the repertoire as a template for first-strand cDNA synthesis. Diversity can be introduced into a region, e.g., CDR3 and/or FR4.

The BSD can also be a sequence that is less than the complete CDR3, e.g. the D segment of a heavy chain CDR3 or a MEBSD. As appreciated by one of skill in the art, when the reference antibody BSD is less than a complete CDR3, a complete CDR3 still results in the antibody expression library, as the remaining CDR3 residues are incorporated into the construct. For example, appropriate oligonucleotides can be designed to incorporate human sequences, e.g., germline J segments, to replace the CDR3 residues that are not part of the MEBSD.

The MEBSD is the region within a CDR3 sequence or a pair of CDR3s that is required to retain the binding specificity of the reference antibody when combined with human sequences that re-constitute the remainder of CDR3 and the rest of the V-region. The MEBSD can be defined empirically or can be predicted from structural considerations.

The antibody library can be a library where the antibody is an IgG, an Fv, a Fab, a Fab', a $F(ab')_2$, a single chain Fv, an IgG with a deletion of one more domains, or any other antibody fragment that includes the V-region.

The antibodies can be displayed on the surface of a virus, cell, spore or virus-like particle. For this purpose, one or both chains of the antibody fragment are typically expressed as a fusion protein, for example as a fusion to a phage coat protein for display on the surface of filamentous phage. Alternatively, the antibodies of the antibody library can be secreted from a host cell.

The following provides an exemplary description using secretion systems to express the antibodies as Fab or Fab' fragments. It is readily apparent to those in the art, however, that the expression systems can be adapted for any library format. For this general example, a library of complete V-regions is constructed by ligation of oligonucleotides encoding CDR3-FR4 segments to the V-segment repertoire as described above. The amplified sequences encoding complete V-regions are cloned into a suitable expression vector and can be fused to constant region sequences at this stage for expression of Fab or Fab' molecules. The antibody fragments can be secreted from prokaryotic or eukaryotic cells including bacteria, yeast, plant cells and mammalian cells.

Filter screening methodologies have been described for detection of secreted antibodies specific for a particular antigen. In one format, the secreted antibody fragments are trapped on a membrane which is probed with soluble antigen (Skerra et al., 1991, *Anal Biochem.* 196:151-5). In this case, bacteria harboring plasmid vectors that direct the secretion of Fab fragments into the bacterial periplasm are grown on a membrane or filter. The secreted fragments are allowed to diffuse to a second "capture" membrane coated with antibody which can bind the antibody fragments (e.g., anti-immunoglobulin antiserum) and the capture filter is probed with specific antigen. Antibody-enzyme conjugates can be used to detect antigen-binding antibody fragments on the capture membrane as a colored spot. The colonies are re-grown on the first membrane and the clone expressing the desired antibody fragment recovered.

Colony lift binding assays have also been described in which the antibodies are allowed to diffuse directly onto an antigen-coated membrane. Giovannoni et al. have described such a protocol for the screening of single-chain antibody libraries (Giovannoni et al., 2001 *Nucleic Acids Research, Vol. 29, No. 5 e27*).

Libraries of secreted antibody fragments can also be screened by ELISA, either using pools of multiple clones or screening of individual clones each secreting a unique antibody sequence. One such method for screening individual clones is described by Watkins et al., 1997, *Anal. Biochem.* 253: 37-45. In this case, microtiter wells were coated with anti-Fab antibody to capture Fab fragments secreted directly in the wells. The Fab samples were then probed with soluble biotinylated antigen followed by detection with streptavidin-alkaline phosphatase conjugates.

Fusion Antibodies

In one embodiment, the polypeptides may be fusion antibodies. In one embodiment, the antibody fragment may comprise one or more C-terminal peptide tags to facilitate detection and purification. In another embodiment the antibody may be fused to a peptide or polypeptide for display on the surface of a cell, spore or virus. For example one chain of the antibody fragment may be displayed as a fusion protein on the surface of a bacteriophage such as a filamentous phage. Methods for display of antibodies on phage are well known in the art and include fusion to pIII and pVIII proteins of a filamentous phage. In a preferred embodiment at least one of the peptides comprising an antibody-phage protein fusion is expressed without a signal peptide in a prl strain of *E. coli* and is presented on the surface of a phage.

The secreted chains may retain the N-terminal methionine (or N-formyl-methionine). Alternatively, and in some cases, depending on the sequence of the antibody, the initial methionine may be removed by proteolytic processing by the host cell.

Embodiments also include other display technology, such as yeast cell display, bacterial cell display, ribosome display, and mammalian cell display. In one embodiment, screening is performed by screening pools of library members.

Fragment and subunit complementation systems can be used in the invention to select/screen for antibodies having desired properties ("complementation system"). In general, fragment complementation systems are comprised of a responder that is fragmented or separated into two (or more) parts that must reassociate to make a functional responder. The fragments/subunits of the responder are fused individually to members of a binding ensemble, and the reassembly of the responder is then driven by the direct or indirect interaction of the two binding ensemble members. In a preferred embodiment the binding ensemble is comprised of an antibody(s) and an antigen(s). Examples of fragment/subunit complementation systems that may be used in the invention are disclosed in U.S. Pat. Nos. 6,342,345, 6,270,964, 6,294,330, 5,503,977, 5,585,245, which are incorporated herein by reference in their entirety, PCT patent application WO 00/71702, and Fields et al., 1989, *Nature* 340:245-247; Bai et al., 1996, *Meth. Enzymol.* 273:331-347, Luo et al., 1997, *Biotechniques* 22:350-352, which are hereby incorporated by reference in their entirety.

Reactivation-based molecular interaction systems (e.g., RAIR™) can be used in the invention to select/screen for antibodies having desired properties ("reactivation system"). In general, reactivation-based molecular interaction systems are comprised of responders, inhibitors, reactivators, and binding ensembles of two or more members. The system has two complexes, one containing the responder, the inhibitor, and a binding ensemble member (the responder complex), and the other containing the reactivator and a binding ensemble member (the reactivator complex). The responder is inhibited in its complex, and docking of the reactivator complex to the responder complex by direct or indirect interaction of the binding ensemble members allows the reactivator to "reactivate" the responder by displacing the inhibitor. Typically, a responder complex comprises a responder molecule, an inhibitor of the responder, and a first binding ensemble member. The components of the responder complex may be arranged in various configurations by covalent or non-covalent linkages. In a preferred embodiment the binding ensemble is comprised of an antibody(s) and an antigen(s).

In a preferred reactivation system, molecular interactions can be detected by a process termed "reactivation of an auto-inhibited responder," or "RAIR" The RAIR systems comprise the following components: a responder complex and a reactivator complex. By auto-inhibited, we mean that the responder is directly linked to the responder so that the base state is automatically inhibited until the inhibitor is displaced and the responder activated by a reactivator complex. Where this linkage is by a covalent bond, the covalent linkages may further comprise a linker. A reactivator complex comprises a reactivator molecule to displace the inhibitor and a second binding ensemble member. Like the components of the responder complex, the reactivator and binding ensemble member may be linked either covalently or non-covalently.

Molecular interaction between the first and the second ensemble members can be detected by the following mechanism: the signal or activity of the responder in the responder complex is sequestered by the inhibitor present in the complex, i.e., the responder is auto-inhibited; when a reactivator complex is introduced, if the second ensemble member in the reactivator complex binds with sufficient affinity to the first ensemble member in the responder complex, the reactivator will be able to displace the inhibitor in the responder complex and lead to the so-called "reactivation of an auto-inhibited responder." The detection of responder activity or signal indicates an interaction between the first and the second ensemble members.

Variations of the RAIR systems can be used for interaction mapping, improving the affinity of a first binding pair member, and isotropic selection of a plurality of binding molecules. In some variations, a third ensemble member may be used.

Examples of reactivation systems are disclosed in U.S. patent application Ser. No. 10/208,730, which is incorporated herein by reference in its entirety.

Systems using molecular sensors activated by competition can also be used in the invention to select/screen for antibodies having desired properties. These systems are designated COMPACT™. In general, competitive activation systems are comprised of a binding ensemble, a responder, and an inhibitor. The responder is complexed with one binding ensemble member and the inhibitor is complexed to another binding ensemble member. The binding ensemble members, upon binding to one another, bring the responder and inhibitor together so that the responder is inhibited. Antibodies of the invention that disrupt the binding ensemble or inhibit binding ensemble formation and thereby activate the responder can then be selected. In a preferred embodiment, the binding ensemble is an antibody(s) and an antigen(s), and the "competitive activator" is an antibody. For example, the binding ensemble antibody might be a reference antibody, and the competitive activator may comprise a library of antibodies which compete with the reference for binding to the antigen. Examples of competitive activation systems that may be used in the invention are disclosed in U.S. patent application Ser. No. 10/076,845, which is incorporated herein by reference in its entirety.

Such a system may further employ a "mask" to control the sensitivity of the system. These systems are described, e.g., in co-pending U.S. application Ser. No. 10/076,845, filed Feb. 14, 2002. A "mask", in the context of a competitive activation system, refers to a molecule that has low affinity for a reporter or inhibitor, such that the mask does not bind appreciably at working concentrations unless it is tethered covalently to the reporter or inhibitor. The mask does not affect reporter activity only the binding of the inhibitor and vice versa. Control of the system with Masks permits a high-affinity inhibitor to be used without fear of increasing the background inhibition because its association rate constant is greatly reduced by the Mask without affecting the dissociation rate constant of the reporter-inhibitor complex, thereby reducing the overall affinity while retaining the stability of the high-affinity reporter-inhibitor complex.

Libraries

In another embodiment of the invention, the secreted polypeptides may be a diverse library of antibodies, antibody fragments, or antibody-related polypeptides with different binding characteristics expressed from a prokaryotic host cell such as a strain of *E. coli* expressing a prl mutation, wherein one or more antibody chain is expressed without a signal peptide. In another embodiment, the secreted polypeptides are expressed in a signal-independent manner. The libraries according to this aspect of the invention show broader representation of VH and VL subclasses.

It is known in the art that different antibodies are secreted at different levels into the periplasm and that certain subclasses of antibody are only poorly secreted in soluble correctly-folded form. In many cases the V-region sequences of the antibody can affect the ability of the antibody to be secreted from *E. coli* Murine V-regions, for example, fold poorly in the periplasm and may lead to the accumulation of aggregated and inactive antibodies (Skerra and Pluckthun, 1991, *Prot. Eng.* 4:971; Bothmann and Pluckthun, 1998, *Nature Biotech.* 18: 376; Helle et al., 1995, *Proc. Natl. Acad. Sci. USA* 92: 11907). Chaperone proteins may improve the folding and expression of some antibody fragments (Bothmann and Pluckthun, 1998, *Nature Biotech.* 18: 376; Bothmann and Pluckthun, 2000, *J. Biol. Chem.* 275: 17100). Bias in secretion of some sub-classes of antibody from bacteria can lead to bias in the sequences of the antibodies which may be screened from a library. An embodiment of the present invention addresses allows for higher yields of functional correctly folded antibodies and antibody fragments from bacterial secretion systems by secretion of antibody chains in a signal-independent manner.

Embodiments of this invention include naïve libraries and immunized libraries. Naïve libraries are made from the B-lymphocytes of a suitable host which has not been challenged with any immunogen, nor which is exhibiting symptoms of infection or inflammation. Immunized libraries are made from a mixture of B-cells and plasma cells obtained from a suitably "immunized" host, i.e., a host that has been challenged with an immunogen. In one embodiment, the mRNA from these cells is translated into cDNA using methods well known in the art (e.g., oligo-dT primers and reverse transcriptase). In an alternative embodiment, nucleic acids encoding antibodies from the host cells (mRNA or genomic DNA) are amplified by PCR with suitable primers. Primers for such antibody gene amplifications are well known in the art (e.g., U.S. Pat. No. 6,096,551, which is incorporated herein by reference in its entirety, and PCT Patent Application WO 00/70023A1 disclose such primers). In a hybrid embodiment, the mRNA from the host cells is synthesized into cDNA and these cDNAs are then amplified in a PCR reaction with antibody specific primers (e.g., U.S. Pat. No. 6,319,690, which is incorporated herein by reference in its entirety, discloses such a hybrid method). Alternatively, the repertoires may be cloned by conventional cDNA cloning technology (Sambrook and Russell, eds, *Molecular Cloning: A Laboratory Manual*, 3rd Ed, vols. 1-3, Cold Spring Harbor Laboratory Press, 2001), without using PCR.

In one embodiment of the invention, a database of published antibody sequences of human origin is established where the antibody sequences are aligned to each other. The database is used to define subgroups of antibody sequences which show a high degree of similarity in both the sequence and the canonical fold of CDR loops (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed, e.g., by total gene synthesis or by the use of synthetic genetic subunits. These genetic subunits correspond to structural sub-elements on the (poly)peptide level. On the DNA level, these genetic subunits are defined by cleavage sites at the start and the end of each of the sub-elements, which are unique in the vector system. All genes which are members of the collection of consensus sequences are constructed such that they contain a similar pattern of corresponding genetic sub-sequences. Most preferably, said (poly)peptides are or are derived from the HuCAL consensus genes: Vk1, Vk2, Vk3, Vk4, Vl1, Vl2, V13, VH1A, VH1B, VH2, VH3, VH4, VH5, VH6, Ck, C1, CH1 or any combination of said HuCAL consensus genes.

This collection of DNA molecules can then be used to create "synthetic libraries" of antibodies, preferably Fv, disulphide-linked Fv, single-chain Fv (scFv), Fab fragments, or Fab' fragments which may be used as sources of specificities against new target antigens. U.S. Pat. No. 6,300,064, which is incorporated herein by reference in its entirety, discloses methods for making synthetic libraries containing more than $10^8$ transformants.

In another embodiment, synthetic human antibodies have now been made by synthesis from defined V-gene elements. Winter (EP 0368 684 B1) has provided a method for amplifying (by PCR), cloning, and expressing antibody variable region genes. Starting with these genes he was able to create libraries of functional antibody fragments by randomizing the CDR3 of the heavy and/or the light chain. This process is functionally equivalent to the natural process of VJ and VDJ recombination which occurs during the development of B-cells in the immune system. For example, repertoires of human germ line $V_H$ gene segments can be rearranged in vitro by joining to synthetic "D-segments" of five random amino acid residues and a J-segment, to create a synthetic third complementarity determining region (CDR) of eight residues: U.S. Pat. No. 5,885,793, which is incorporated herein by reference in its entirety, discloses methods of making such antibody libraries such as these that create libraries containing $10^7$ phage clones.

The antibody fragments according to this aspect of the invention may be soluble secreted antibody fragments or may be presented as a fusion protein on the surface of a cell, spore or virus. Thus, for example, the library of antibodies may be a phage-display library in which one or more chains of the antibody fragment are expressed as a fusion protein with a phage protein in which at least one of the peptides comprising the fusion protein is expressed without a signal peptide. If the antibody fragment is comprised of a heavy and a light chain, it is preferred that both chains are expressed without a signal peptide. In this aspect of the invention the host strain is chosen to be suitable for expression of the antibody library and may be a mutant strain such as prlA4 or may be a strain chosen for another purpose, for example a strain with high transformation frequency, in which the mutant prl protein is expressed from a plasmid expression vector.

Both pIII and pVIII have been used to display peptide and antibody libraries. Display of nonimmune or "naïve" antibody-phage libraries on pIII has been used to isolate human antibodies against a variety of target antigens. Antibodies can be isolated in either scFv or Fab formats, the scFv or one of the Fab chains being fused at the N-terminus of the phage protein. In all cases described previously, a signal peptide is fused at the N-terminus of the antibody chain in order to direct secretion of the antibody-phage fusion protein. The other proteins of the phage coat have also been used to display antibody chains. pVII and pIX have been used to display the antibody variable heavy-chain region ($V_H$) and variable light-chain region ($V_L$), respectively. pIX display has also been used to construct a naïve human antibody library based on the fusion of scFv to the N terminus of pIX using a PelB signal peptide for secretion (Gao et al., 2002, Proc. Natl. Acad Sci 99: 12612). Because of the high efficiency of phage transduction, phage-displayed antibody libraries can be large, with diversities in excess of $10^9$ antibody molecules or sometimes in excess of $10^{10}$ or even $10^{11}$ antibodies per library.

In some embodiments, the library can be a library of epitope-focused human antibodies as described in U.S. patent application Ser. No. 11/040,159, filed Jan. 20, 2005, which is incorporated herein by reference in its entirety. For example, such a library can comprise a plurality of nucleic acids that encode a diverse population of heavy chain V segments, wherein the V segments are not linked to a CDR3. The invention also provides a library comprising nucleic acids that encode a diverse population of light chain V segments, wherein the V segments are not linked to a CDR3. The V segments of either or both libraries can be, e.g., human germline. Libraries of epitope-focused human antibodies can range in size from $10^3$ to $10^5$ antibodies per library.

Antibody libraries may also be focused libraries comprising predominantly members of one or more sub-class of VH or VL gene segments. Thus, for example, in humans there are 7 recognized VH sub-classes (VH1-VH7) and 16 VL sub-classes (Vkappa1-Vkappa6 and Vlambda1-Vlambda10) and a focused library may be constructed comprising members of one or more VH sub-class in combination with a diverse library of Vkappa chains or Vlambda light chains. Alternatively, a focused library of one or more VL sub-classes may be combined with a diverse library of heavy chains. As a further alternative, a focused library may be constructed comprising predominantly members of a single VL sub-class and a single VH sub-class. Antibody fragments of the VH3 sub-class are typically expressed efficiently in E. coli when expressed in a signal-dependent fashion. Antibodies of other VH sub-classes are not efficiently secreted using signal peptides. Similarly, antibody fragments with murine V-regions are poorly secreted using signal peptides. The present invention allows improved representation of secreted antibodies of different sub-classes and allows efficient secretion of antibody libraries comprising murine V-regions.

In another embodiment, the invention provides a library comprising a plurality of human antibody V-region pairs where a V-region pair comprises: i) an unselected heavy chain V-region comprising a human V segment and a heavy chain CDR3 from a reference antibody, and ii) an unselected light chain V-region comprising a human V segment and a light chain CDR3 from the reference antibody.

In other embodiments, the library is a library comprising nucleic acids encoding human antibody V-region pairs, where the VH and VL V segments are each linked to a MEBSD from a reference antibody of interest.

A library of the invention can also comprise nucleic acids encoding a plurality of VH or VL regions, wherein the VH or VL regions comprise V segments from one VH or VL sub-class, wherein the V regions lack D and/or J segments. In one embodiment, the V segments of the VH regions are germline and/or the V segments of the VL regions are germline.

The invention also provides a library comprising a plurality of antibody V region pairs, wherein a pair comprises: i) a heavy-chain V region comprising a binding specificity determinant BSD from a heavy chain CDR3 from a reference antibody joined to a diversity of V segments, and ii) a light chain V region comprising a BSD from a light chain CDR3 from the reference antibody joined to a diversity of V segments, wherein at least one of the BSDs comprises less than the reference antibody CDR3.

Multimeric Proteins

Proper assembly of polypeptide subunits of a multimeric protein to form a stable complex is requited to ensure the biological function of the multimeric protein. An embodiment of the present invention enables expression, secretion and assembly of selected monomeric polypeptides to effect efficient production of heteromultimers outside of the cytoplasm. One or more of the monomer polypeptides of the multimeric protein can be made without a signal sequence in the methods of the invention, and the other monomer polypeptides can be expressed with or without signal sequence(s). Assembled multimeric proteins that may be produced by the present invention include antibodies, antibody fragments or antibody-related polypeptides.

Nucleic Acids

The nucleic acid sequences that are useful in the methods of this invention, i.e., those that encode at least in part the individual peptides, polypeptides and proteins secreted in the method of the invention, or those expressed in or comprising the libraries of this invention, may be native, synthetic or a combination thereof. They may be mRNA, DNA or cDNA. In the preferred embodiment, the nucleic acids encode antibodies.

Recombinant DNA methodologies may be used to create antibody fragments that cannot be made by enzymatic digestion. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., 1990, *Nature* 348:552-554). Nucleic acids encoding the polypeptides of the invention can be obtained using routine techniques in the field of recombinant genetics (see, e.g., Sambrook and Russell, eds, 2001, *Molecular Cloning: A Laboratory Manual*, 3rd Ed, vols. 1-3, Cold Spring Harbor Laboratory Press; and Ausubel, ed., 1997, *Current Protocols in Molecular Biology*, John Wiley & Sons, Inc. New York).

Often, the nucleic acid sequences encoding the polypeptides of the invention are cloned from cDNA or genomic DNA libraries by hybridization with probes, or isolated using amplification techniques with oligonucleotide primers. Amplification techniques can be used to amplify and isolate sequences from DNA or RNA (see, e.g., Dieffenbach & Dveksler, 1995, *PCR Primers: A Laboratory Manual*). Alternatively, overlapping oligonucleotides can be produced synthetically and joined to produce one or more of the domains. Nucleic acids encoding the component domains can also be isolated from expression libraries using antibodies as probes.

In an example of obtaining a nucleic acid encoding a polypeptide of the invention using PCR, the nucleic acid sequence or subsequence is PCR amplified, using a sense primer containing one restriction site and an antisense primer containing another restriction site. This will produce a nucleic acid encoding the desired polypeptide and having terminal restriction sites. This nucleic acid can then be easily ligated into a vector having the appropriate corresponding restriction sites. If the desired polypeptide is a fusion protein, the domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the polypeptide encoding sequence of the invention is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as U.S. Pat. No. 4,683,202, which is incorporated herein by reference in its entirety; Innis et al., eds, 1990, *PCR Protocols A Guide to Methods and Applications*, Academic Press. Inc. San Diego, Calif.; Arnheim & Levinson, 1990, *C&EN* 36-47, *The Journal Of NIH Research* 3: 81-94; Kwoh et al., 1989, *Proc. Natl. Acad. Sci. USA* 86: 1173; Guatelli et al., 1990, *Proc. Natl. Acad. Sci. USA* 87, 1874; Lomell et al., 1989, *J. Clin. Chem.*, 35: 1826; Landegren et al., 1988, *Science* 241: 1077-1080; Van Brunt, 1990, *Biotechnology* 8: 291-294; Wu and Wallace, 1989, *Gene* 4: 560; and Barringer et al., 1990, *Gene* 89: 117.

In some embodiments, it may be desirable to modify the polypeptides of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith, 1979, *Gene* 8:81-97, Roberts et al., 1987, *Nature* 328: 731-734.

In some embodiments, the recombinant nucleic acids encoding the polypeptides of the invention are modified to provide preferred codons which enhance translation of the nucleic acid in a selected organism (e.g., yeast preferred codons are substituted into a coding nucleic acid for expression in yeast).

The polynucleotides of the invention also include polynucleotides including nucleotide sequences that are substantially equivalent to the polynucleotides of the invention. Polynucleotides according to the invention can have at least about 80%, more typically at least about 90%, and even more typically at least about 95%, sequence identity to a polynucleotide of the invention. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

The nucleic acids useful in this invention may be naturally diverse, synthetic diversity may be introduced into those naturally diverse members, or the diversity may be entirely synthetic. For example, synthetic diversity can be introduced into one or more CDRs of antibody genes. Preferably, it is introduced into CDR1 and CDR2 of immunoglobulins. Preferably, natural diversity is captured in the CDR3 regions of the immunoglobulin genes of this invention from B cells. Most preferably, the nucleic acids of this invention comprise a population of immunoglobulin genes that comprise synthetic diversity in at least one, and more preferably both of the CDR1 and CDR2 and diversity in CDR3 captured from B cells.

Nucleic acids which encode protein analogs in accordance with this invention (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., 1989, *Molecular Cloning: A Laboratory Manual*, Cold Spring Harbor Laboratory Press, Cold Spring Harbor, N.Y. and/or Ausubel et al., editors, 1994, *Current Protocols in Molecular Biology*, Green Publishers Inc. and Wiley and Sons, N.Y. Chemical synthesis using methods described by Engels et al., 1989, in *Angew. Chem. Intl. Ed.*, Volume 28, pages 716-734, may also be used to prepare such nucleic acids.

"Recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides or chimeric polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., 1983, *DNA* 2:183. A versatile and efficient method for producing site-specific changes in a polynucleotide sequence was published by Zoller and Smith, 1982, *Nucleic Acids Res.* 10:6487-6500.

PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the collagen at the position specified by the primer. The product DNA fragments replace the corresponding region in the plasmid and this gives the desired amino acid variant.

A further technique for generating amino acid variants is the cassette mutagenesis technique described in Wells et al., 1985, *Gene* 34:315; and other mutagenesis techniques well known in the art, such as, for example, the techniques in Sambrook et al., supra, and *Current Protocols in Molecular Biology*, Ausubel et al.

Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions. In addition, nucleic acids encoding the same amino acid sequence as that of the polypeptide of the invention but having very different nucleic acid sequences due to the degeneracy of the genetic code are also encompassed within the invention.

Host Cells

Another aspect of the invention provides a prokaryotic host cell allowing for secretion of antibodies or antigen-binding antibody fragments or multimeric proteins without the need for a signal peptide. Strains suitable for use in the invention do not have a generally increased permeability but selectively secrete proteins naturally destined for secretion including the antibodies and antibody fragments of the invention. In a preferred embodiment, the prokaryote is preferably a gram-negative bacterium, and most preferably is the bacterium *E. coli*.

Multiple pathways have been described in Gram-negative bacteria for the secretion of proteins from the cytoplasm either to the periplasm or through both the inner and outer membranes, traditionally grouped into four different systems. The Type III and Type IV systems are generally used for direct transfer of bacterial proteins to adjacent eukaryotic host cells. The Type I system forms a "tunnel" that links the outer and inner membranes such that proteins exported by this pathway are secreted directly into the extracellular medium. The Type II secretion system, also known as the general secretory pathway or Sec pathway, is responsible for the secretion of the majority of proteins through the inner membrane into the periplasm. An additional secretion system, which also makes use of specific N-terminal signal peptides to direct secretion of proteins via the periplasm, is the twin-arginine translocation (TAT) pathway. In contrast to the Sec system, which secretes loosely folded proteins to the periplasm where protein assembly takes place, the TAT pathway is used for the secretion of already folded enzymes (reviewed by Berks et al., 2005, *Current Opinion* 8: 174-181).

The Type II secretion system has been widely used for the secretion of recombinant proteins from *E. coli*. In an embodiment of the invention, the host cells comprise a mutant gene(s) in the Type II, or Sec, pathway. The addition of a short N-terminal signal sequence to the recombinant protein serves to direct the recombinant protein to this secretion pathway and the signal peptide is removed during the secretion process. The pathway has been used to express antibody fragments such as Fab fragments directed by signal sequences from bacterial proteins naturally secreted using this pathway, including OmpA, PelB and PhoA. The antibody heavy and light chains have been shown to assemble in the periplasm to form antigen-binding Fab fragments (e.g., Skerra and Pluckthun, 1991, *Protein Eng.* 4: 971-979).

The translocation machinery of the Sec pathway is a well-studied enzyme complex, the translocase, which consists of several integral membrane proteins and an associated ATPase to provide the energy for translocation (reviewed in Fekkes and Driessen, 1999, *Microbiology and Molecular Biology Reviews*, 63: 161-173; van der Wolk et al., 1998, EMBO J. 17: 3631-3639). The core of this enzyme complex consists of the membrane-embedded heterotrimer consisting of the SecY, SecE and SecG proteins (the SecYEG complex), and the peripheral homodimeric ATPase SecA. The SecD, SecF and YajC proteins form a separate heterotrimeric complex that associates with the SecYEG complex to form the complete translocase.

Newly synthesized precursor proteins are bound by the chaperone SecB which stabilizes the pre-protein in a loosely folded conformation competent for translocation. SecB and the signal sequence target the pre-protein to the membrane, and both associate with SecA which is bound with high affinity to the SecY subunit of the SecYEG complex. As a result of the SecB-SecA interaction, the pre-protein is transferred to SecA, which binds both its signal sequence and its mature domain. The release of SecB from the membrane requires the binding of ATP at one of the two ATP-binding sites of SecA. At this stage, a loop of the signal sequence and the N-terminal region of the pre-protein are presented to the periplasmic face of the membrane, allowing cleavage of the signal sequence by leader peptidase.

The N-terminal signal sequence of pre-proteins has been regarded as important for the initial targeting event, the recognition of the pre-protein by SecA. Aberrant signal sequences are not efficiently recognized by the translocase resulting in a deficiency in translocation.

The Type I secretion system has also been used to direct the secretion of heterologous proteins from *E. coli*. In an embodiment of the invention, the host cell comprises a mutant gene in the Type I secretion system. The secretion signals recognized by the components of the Type I pathway are located at the carboxy terminus of the secreted protein and, in most cases, the secretion signals are not cleaved off either during or after secretion. A well-characterized *E. coli* protein secreted via the Type I secretion pathway is alpha-hemolysin. The signal sequence from this protein has been used to direct the secretion of a number of heterologous proteins including a scFv antibody fragment by fusion of the C-terminal region of hemolysin to the C-terminus of the scFv coding region (Fernandez and Lorenzo, 2001, *Mol. Microbiology* 40: 332-346). In this case the C-terminal hemolysin signal peptide was retained in the secreted product.

Several mutations in the Sec system components are known which allow efficient secretion of normally secreted *E. coli* proteins with defective or absent signal sequences. Such protein localization (prl) mutations have been identified in multiple components of the Sec system, including for example, SecY (prlA), SecE (prlG), SecG (prlH) and SecA (prlD) (Bost and Belin, 1997, *J. Biol Chem.* 272:4087-93, which is incorporated herein by reference in its entirety).

It has also been found that prl mutations can rescue secretion of some naturally secreted *E. coli* proteins in the complete absence of a signal peptide. Thus *E. coli* maltose binding protein and alkaline phosphatase lacking a signal peptide have been secreted from prlA mutants (Derman et al., 1993, *EMBO J.* 12: 879). The bacteriophage protein LamB can also be secreted without a signal sequence in prlA mutants (Flower et al., 1994, *J Bacteriol* 176: 18). However, heterologous proteins such as eukaryotic proteins have not been previously shown to be secreted without a signal sequence from prl strains. Wong et al., 1988, *Gene* 68: 193) achieved successful secretion of insulin-like growth factor-1 from *E. coli* using the signal sequences from the LamB or OmpF genes and showed that the processing efficiency of LamB-IGF-1 and OmpF-IGF-1 was enhanced in a strain bearing the prlA4 mutation. Human CD4 fused to OmpA, PhoA, or OmpF signal peptides has also been shown to express efficiently in prlA mutants (Rockenbach et al., 1991, *Appl Microbiol Biotechnol.* 35:32-7). Overexpression of SecY mutant proteins on a plasmid vector has also been explored for enhancing expression of a human protein from *E. coli*. Thus overexpression of the prlA4 mutant SecY protein together with secE increased secretion of human IL-6 fused to the OmpA signal peptide (Perez-Perez et al., 1994, BioTechnology 12: 178).

PrlA strains have also been used to improve diversity of peptides displayed on surface of filamentous phage fd using the pIII signal peptide (Peters et al., 1994, *J. Bacteriol.* 176: 4296) and to express bovine pancreatic trypsin inhibitor as a phage fusion protein from a PhoA signal peptide (U.S. Pat. No. 5,223,409, which is incorporated herein by reference in its entirety; Ladner et al.). Thus it appears that prlA mutant proteins can facilitate the expression of certain eukaryotic proteins expressed in a signal-peptide-dependent manner.

Proteins that are normally secreted from cells often form insoluble inclusion bodies when recombinantly expressed in *E. coli* without a signal sequence. For example, genes encoding antibody heavy and light chains or antibody fragments have been expressed without signal sequences in *E. coli* and the proteins produced typically accumulate as insoluble products in inclusion bodies inside the cell (Boss et al., 1984, *Nucl. Acids Res* 12: 3791; Cabilly et al., 1984 *Proc. Natl. Acad. Sci. USA* 81:3273). Such proteins are not available for transport across the cytoplasmic membrane and do not form functional protein. Methods for re-folding antibody fragments from inclusion bodies are provided in U.S. Pat. Nos. 6,331,415 and 4,816,567. However, such methods for generating antibodies are inefficient and provide poor yields of functional antibody and cannot be used for library screening purposes.

In a preferred embodiment of the invention, the prokaryotic host cell contains a prl mutation in one or more components of the secretory apparatus which allows secretion of the antibody in the absence of an encoded signal peptide. The prl mutant is a mutation which permits secretion of signal-less monomeric proteins and may comprise a mutation affecting the activity of a SecY, SecA, SecE or SecG gene or another gene. Prl mutants also permit secretion of proteins encoded with a signal peptide in a signal-independent fashion. One embodiment of the invention comprises secreting an antibody polypeptide with a signal sequence in a host strain with a prl mutation and achieving assembly of the antibody into a functional multimeric protein. This is an unexpected result since secretion and chain assembly are thought to be closely coordinated. Another embodiment comprises secreting a polypeptide lacking a signal sequence in a host strain with a prl mutation. Preferably the prl mutation comprises a mutation in SecY (prlA) or SecE (prlG). Most preferably the prl mutant comprises one or more mutations in SecY such as the prlA4 mutant strain (Emr and Bassford, 1982, *J. Biol Chem* 257: 5852-5860). The prlA4 allele contains two missense mutations in the secY gene, resulting in the amino-acid substitutions F286Y and I408N. Most preferably, the prlA mutant comprises at least an I408N mutation in SecY. The sequence of the prlA4 mutant SecY protein is shown in FIG. 1.

The prl mutant may contain a prl mutation in the chromosome of the host strain, such as the prlA4 mutant strain of *E. coli*. Alternatively, the prl mutant may be derived by overexpression of an additional copy of a mutant Sec gene, for example, by expression in a plasmid-based expression vector. Thus, for instance, the prl mutant may comprise a mutant SecY or SecE gene expressed on a plasmid. Such a plasmid may be constructed using a constitutive or an inducible promoter allowing for induction of secretion of polypeptides without signal sequences only at desired times. Methods for regulating expression in *E. coli* are well known in the art and include the use of inducible promoters such as the lac, trc, or tac promoters which are inducible by IPTG, and arabinose-inducible promoters. The mutant Sec gene may be a mutant Sec gene from *E. coli* or from another gram-negative bacterium. Thus, for example, the prlA4 mutant form of SecY may be expressed from a plasmid in an *E. coli* host cell in order to permit secretion of a Fab fragment expressed without a signal peptide.

The host cell may be a wild type *E. coli* strain such as W3110 or may be another strain of *E. coli*. Suitable host strains include TOP10, DH5, DH5alpha, Origami and HB101. The host cell may be chosen to provide mutations in other chaperones and genes which affect the folding, assembly and secretion of heterologous proteins. It has been demonstrated that a combination of molecular chaperones such as bacterial DnaK and GroE systems, can augment refolding of proteins that interact with the chaperonins yet fail to fold properly (Buchberger, A., Schroder, H., Hesterkamp, T., Schonfeld, H. J., and Bukau, B., 1996, *J. Mol. Biol.* 261, 328-233, Petit, M. A., Bedale, W., Osipiuk, J., Lu, C., Rajagopalan, M., McInerney, P., Goodman, M. F., Echols, H., 1994, *J. Biol. Chem.* 269, 23824-23829). DnaK also cooperates with Trigger Factor in folding of newly synthesized proteins.

Library embodiments of this invention may be expressed in prl mutant strains in order to allow secretion for screening of antibody fragments in various functional assays. The identical vectors may also be expressed in alternative strains of *E. coli* for expression within the cytoplasm without the need to re-engineer the antibody molecules. Intracellular expression may be used for efficient production of antibody fragments, for example using trxB gor mutants to provide an oxidizing cytoplasm to allow disulphide-bond formation. High level expression of correctly folded and assembled Fab fragments can be achieved in the cytoplasm of *E. coli* carrying mutations in the glutathione oxidoreductase (gor) and the thioredoxin reductase (trxB) genes (Venturi et al., 2002, *Mol Biol.* 315:1-8). Expression and assembly of correctly folded antibody fragments can be further enhanced using coexpression of molecular chaperones (Levy et al., 2001 *Protein Expr Purif.* 23: 338-47; Jurado et al., 2002 *J. Mol Biol.* 28: 320:1-10).

Another embodiment of the invention includes mutants in a second secretory pathway, the twin arginine translocation or TAT pathway. It is intended that all tat-dependent signal peptides are to be encompassed by the present invention. Specific examples include but are not limited to the phoD and the lipA sequences.

Another embodiment of the invention includes mutants in a third secretory pathway, referred to as the Type III secretion system. Type III secretion machinery is present in numerous gram-negative bacteria (including members of the species *Shigella, Salmonella, Yersinia, Escherichia, Pseudomonas, Xanthomonas, Ralstonia,* and *Erwinia*) that are pathogenic for man, animals, and plants. For example, the Sec-independent type III secretion pathway is involved in secretion of *Yersinia* anti-host proteins. In *Salmonella* and *Shigella* species, it is involved in the process of entry into epithelial cells. It is also implicated in EPEC signal transducing proteins, *Pseudomonas aeruginosa* toxins, and virulence factors of many plant pathogens, as well as in flagellum assembly of bacteria such as *S. typhimurium* and *Bacillus subtilis*.

Features of this secretion pathway can include activation of secretion by contact of the bacterium with host cells (Menard et al., 1994, The secretion of the *Shigella flexneri* Ipa invasins is activated by epithelial cells and controlled by IpaB and IpaD, *EMBO J.,* 13:5293-5302; Watarai et al., 1995, Contact of *Shigella* with host cells triggers release of Ipa invasins and is an essential function of invasiveness, *EMBO J.,* 14:2461-2470; Zierler and Galan, 1995, Contact with cultures epithelial cells stimulates secretion of *Salmonella typhimurium* invasion proteins InvJ, *Infect. Immun.,* 63:4024-4028); that some of the secreted proteins are delivered into the cytoplasm of host cells (Rosqvist et al., 1994, Target cell contact triggers expression and polarized transfer of *Yersinia* YopE cytotoxin into mammalian cells, *EMBO J.,* 13:964-972; Sory and Cornelis, 1994, Translocation of an hybrid YopE-adenylate-cyclase from *Yersinia enterocolitica* into HeLa cells, Mol. Microbiol., 14:583-594; Wood et al, 1996, SopE, a secreted protein of *Salmonella dublin*, is translocated into the target eukaryotic cell via a sip-dependent mechanism and promotes bacterial entry, Mol. Microbiol., 22:327-338; Collazo and Galan, 1997, The invasion-associated type III system of *Salmonella typhimurium* directs the translocation of Sip proteins into the host cell, Mol. Microbiol, 24:747-756); and that transcription of genes encoding secreted proteins is controlled by secretion of regulatory proteins (Hughes et al., 1993, Sensing structural intermediates in bacterial flagellar assembly by export of a negative regulator, *Science,* 262: 1277-1280; Pettersson et al., 1996, Modulation of virulence factor expression by pathogen target cell contact, *Science,* 273:1231-1233).

In another embodiment of this aspect of the invention, the host strain may be selected for other mutations impacting secretion. For this purpose, a secreted selectable marker protein is expressed without a signal peptide in the host cell and mutants are selected which permit secretion of the marker protein. The host strain may be treated with a mutagen to increase the number of mutations or another method to introduce mutations may be used such as transposon mutagenesis. A suitable marker protein is beta-lactamase, which confers resistance to beta-lactam antibiotics such as ampicillin. Beta-lactamase is expressed without a signal peptide and ampicillin-resistant mutants are selected. These mutants are screened for the ability to secrete other proteins such as antibody fragments in the absence of signal peptides in order to identify prl mutations. By this means, a mutation allowing secretion without a signal sequence can be introduced into any desired strain of E. coli such as a wild-type W3110 strain or a strain with a high transformation frequency or a strain with mutations in other chaperone proteins.

Some embodiments of the invention use singly or multiply protease-deficient mutant hosts. Different proteins will be more or less sensitive to different proteases normally produced by the microorganisms. Strains may be used which are deficient in proteases such as ompT and degP, Protease III, La Protease, ClpYQ, ClpXP and ClpAP.

This invention will be better understood from the Experimental Details which follow. However, one skilled in the art will readily appreciate that the specific methods and results discussed are merely illustrative of the invention as described more fully in the claims which follow thereafter.

EXAMPLES

Example 1

Expression and Secretion of Human Anti-PcrV Fab Fragment without Signal Peptides The Fab fragment of human antibody 1A8 was expressed and secreted from E. coli mutant prlA4 without signal peptides. Fab 1A8 is an engineered human antibody fragment which binds specifically to an epitope on the PcrV protein of Pseudomonas aeruginosa with high affinity. It competes for binding with a mouse antibody Mab166 identified to the same epitope (Frank et al, 2002, J Infect Dis. 186:64-73). The light chain of 1A8 consists of a Vk1-kappa light chain and the Fd chain is a VH3 sub-class V-region fused to an IgG1 CH1 domain.

A signal-less expression vector for the expression of Fab 1A8 was derived from pGEX-4T-1 (GE Healthcare) as follows. The Ampicillin-resistance gene in pGEX-4T-1 was deleted by digestion with AatII and AlwNI, and was replaced with a Chloramphenicol resistance gene obtained by PCR amplification from plasmid pACYCDuet (Novagen) to form pGEX-CAT. A point mutation of T to A at position 256 was generated by PCR-mutagenesis to introduce a unique Bst1107I restriction site in pGEX-CAT just before the translation initiation codon downstream of the pTac promoter.

The pTac promoter of pGEX-CAT was used to express the light chain which was cloned between the Bst1107I and EcoRI sites by PCR using following primers to give vector KB-L. A T7 terminator sequence was incorporated in the Primer 2 before the EcoRI site.

Primer 1:                           (SEQ ID NO: 4)
GGAAACAGTATACATGGACATCCAGTTGACCCAGTC Primer 2:                           (SEQ ID NO: 5)
GCCAGTGAATTCAAACCCCTCAAGACCCGTTTAGAGGCCCCAA

GGGGTTATGCTAGTTAATCGATTTAACACTCTCCCCTGTTGAAGCTC

This primer pair amplifies the mature light-chain coding sequence of 1A8 and adds a translation-initiation codon and an upstream sequence to provide an appropriate distance between the Shine-Dalgarno ribosome-binding sequence (AGGA (SEQ ID NO:6)) and the initiation codon of 9 nucleotides. The predicted amino acid sequence of the N-terminus of the light chain (in single-letter amino-acid code) is:

MDIQLTQ             (SEQ ID NO: 7)

The heavy chain (Fd chain) of Fab 1A8 was cloned similarly by PCR, using primers 3 and 4, and introduced between the Bst1107I and NotI sites of pGEX-CAT to give vector KB-H.

Primer 3:                           (SEQ ID NO: 8)
GGAAACAGTATACATGGAGGTGCAGCTGGTGGAGTC Primer 4:                           (SEQ ID NO: 9)
CACGATGCGGCCGCTTAACAAGATTTGGGCTCAACTTTC This primer pair amplifies the mature Fd chain coding sequence and adds a translation-initiation codon and sequences to provide a Shine-Dalgarno-ATG distance of 9 nucleotides. The predicted amino acid sequence of the N-terminus of the heavy chain is:

MEVQLVE             (SEQ ID NO: 10)

The pTac expression cassette of KB-H was then amplified by PCR using Primer 4 and 5 and cloned into KB-L between EcoRI and NotI sites to give vector KB-LH.

Primer 5:                           (SEQ ID NO: 11)
CGATGCGAATTCGACTCTAGCGCTGTGGTATGGCT

GTGCAGGTCG

The final signal-less expression vector for expression of Fab 1A8 was constructed by cloning the EcoRI and FspI fragment (138 nucleotides) of pUC19 (Fermentas) into KB-LH between EcoRI and AfeI sites to provide a spacer between 2 pTac expression cassettes. A map of the plasmid KB5246 is shown in FIG. 2.

E. coli strain SE6004, containing the prlA4 mutation (Emr et al., 1982, J. Biol. Chem 257: 5852; Wong et al., 1988, Gene 68: 193), was obtained from the Netherlands Culture Collection of Bacteria (NCCB catalog number 2976).

Plasmid KB5246 was introduced into SE6004 by electroporation. Electro-competent cells were prepared using standard techniques as described in Short Protocols in Molecular Biology (3$^{rd}$ edition), Ausubel et al., (John Wiley and Sons Inc). Electropration was carried out using a Biorad E. coli Pulser electroporation apparatus according to the manufacturer's instructions with a 1.8 kV pulse and a 5 ms time constant. Electroporation cuvettes were from BTX. Transformants selected on 34 µg/ml chloramphenicol were cultured in 2×YT medium and expression of the heavy and light chains of Fab1A8 was induced using isopropyl-beta-D-thiogalactopyranoside (IPTG) at concentrations up to 1 mM. Induction was carried out for 3 hours for analysis of Fab expression in the periplasm, or cultured for 16 hours for analysis of Fab released into the medium.

For analysis of Fab secreted across the cytoplasmic membrane into the periplasm, cells were fractionated as follows. The bacterial cell pellet from a 1 liter culture was resuspended in 10 ml of TES buffer (0.2M Tris pH 8.0, 17.12% sucrose and 0.5 mM EDTA) and incubated at 4° C. for 15 minutes. After the addition of 12.5 ml of TES/$H_2O$ at a ratio of 1/4, the cell mixture was incubated at 4° C. for a further 15 minutes. The cells were pelleted by centrifugation at 7000 rpm in a Sorvall bench-top centrifuge for 15 minutes and the supernatant was kept. The pellet was then resuspended in 10 ml TES supplemented with 15 mM $Mg_2SO_4$ and incubated at 4° C. for 10 minutes followed by repelleting at 7000 rpm and retention of the supernatant.

Figure 3:
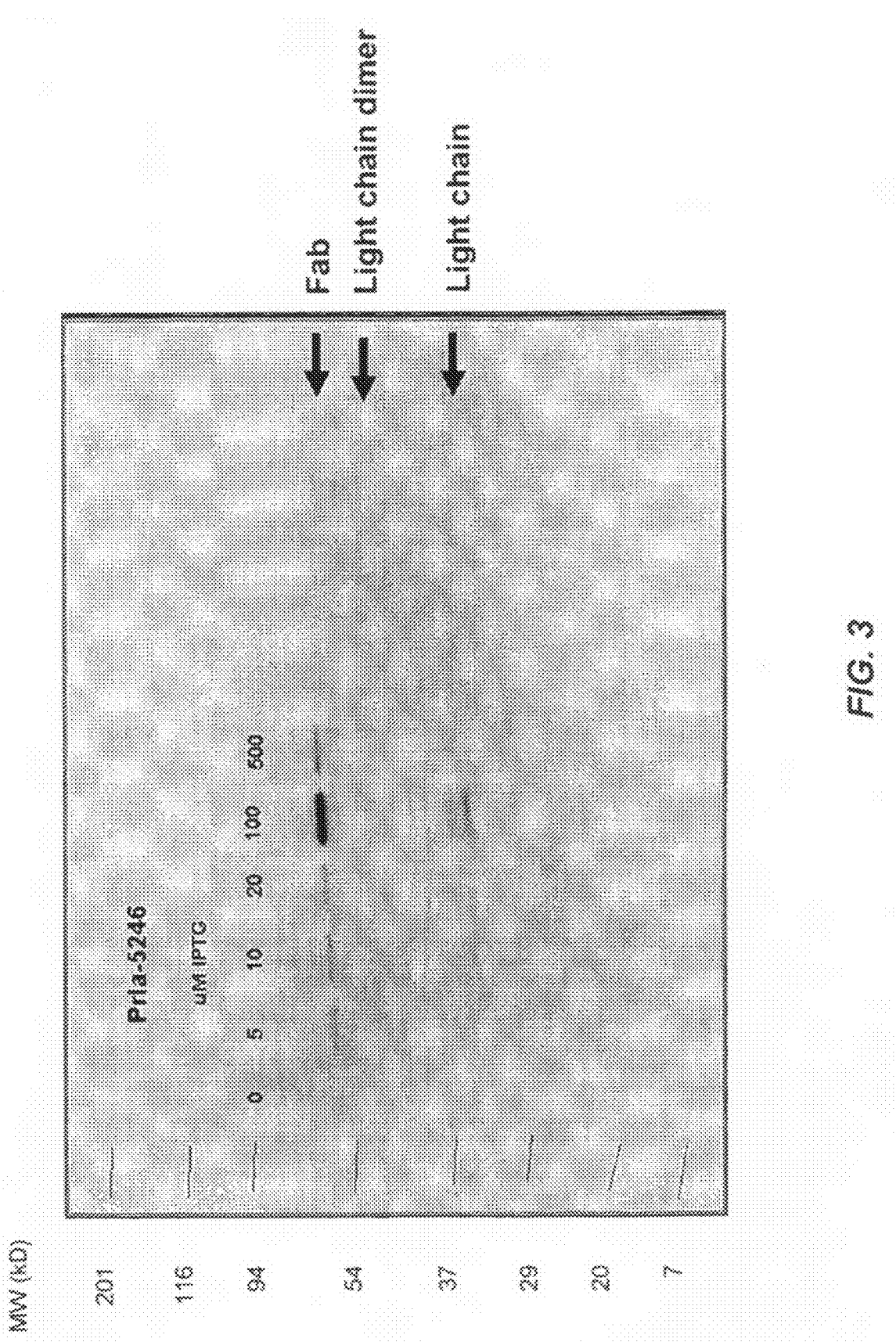
FIG. 3 shows a western blot analysis showing secretion of assembled Fab 1A8 in periplasmic fractions of SE6004 transformed with plasmid KB5246. Fab expression was induced by the addition of IPTG (SEC) ID NO:2) at the concentrations shown (in µM). Samples were run on SDS-PAGE gel under non-reducing conditions, and probed using an anti-Human Kappa specific antibody conjugated to Horseradish peroxidase.

10 µl of periplasmic extract was run on an SDS-PAGE gel under non-reducing conditions, transferred to PVDF membrane and western blotted using an anti-Human Kappa specific antibody conjugated to Horseradish peroxidase (Zymed labs). The Peroxidase substrate ECL plus (GE Healthcare) was use to produce luminescent signal which was then detected on radiographic film to detect Fab secretion. FIG. 3 shows a representative Western blot demonstrating secretion of assembled 1A8 Fab detected in the periplasm. A small amount of immunoglobulin-related protein of lower molecular weight is also detectable. These bands are consistent with the secretion of light-chain dimers and monomeric light chain as typically found on secretion of Fab fragments from E. coli in other, signal-dependent secretion systems.

Fab 1A8 secreted either into the periplasm or into the medium was analyzed for antigen-binding activity using a specific antigen-based enzyme-linked immunosorbent assay (ELISA). For this purpose, recombinant PcrV antigen, cloned as a fusion protein in frame with an amino terminal glutathione S-transferase (GST) purification tag, was used as described previously (Frank et al., 2002, *J. Infectious Diseases* 186: 64-73). The PcrV coding sequence is cloned in the expression vector pGEX 2TK (GE Healthcare) to generate the GST-PcrV fusion protein.

For production of antigen for use in ELISA for the detection of functional anti-PcrV Fabs, GST-PcrV fusion protein was expressed from E. coli (BL21) transformed with pGEX 2TK-PcrV and purified as follows. 4 liter liquid culture batches of E. coli expressing GST-PcrV were grown in 2×YT medium to an optical density of 0.6 at 600 nm before induction of protein expression with 0.5 mM IPTG and a further 3 hours growth. The bacterial cells were pelleted by centrifugation and lysed in a solution of Bug Buster (Novagen) supplemented with 1 U/ml rLysozyme (Novagen) and a protease inhibitor cocktail (Sigma-Aldrich) diluted to the manufacturer's instructions. After clearing the lysate by centrifugation and filtration, it was passed over a glutathione sepharose column (GSTrap FF, GE Healthcare), washed and the pure GST-PcrV was eluted in 10 mM Glutathione. The antigen was desalted back into PBS.

Antigen-binding ELISAs for detection of anti-PcrV Fab in periplasm fractions or in medium samples were carried out as follows. ELISA plates (Costar EIA/RIA) were coated with 100 ng/well GST-PcrV in PBS (see above) by incubating at 4° C. for 16 hours and blocking for 1 hour with a 5% solution of non-fat dry milk in PBS 0.1% Tween 20 (PBST). Periplasmic fraction samples were diluted in a 2 fold series and applied to the ELISA plate for 1 hour at 33° C. After washing with PBST, antibody fragments binding to the antigen were detected with goat anti-human kappa-HRP conjugate (US Biological) at a dilution of 1/1000 in PBST. Antibody binding was revealed using the peroxidase substrate Tetramethyl benzidine (TMB) (100 µl/well), and the reaction was stopped with the addition of 100 ul 2N $H_2SO_4$ and read by a standard plate-reader.

Figure 4:
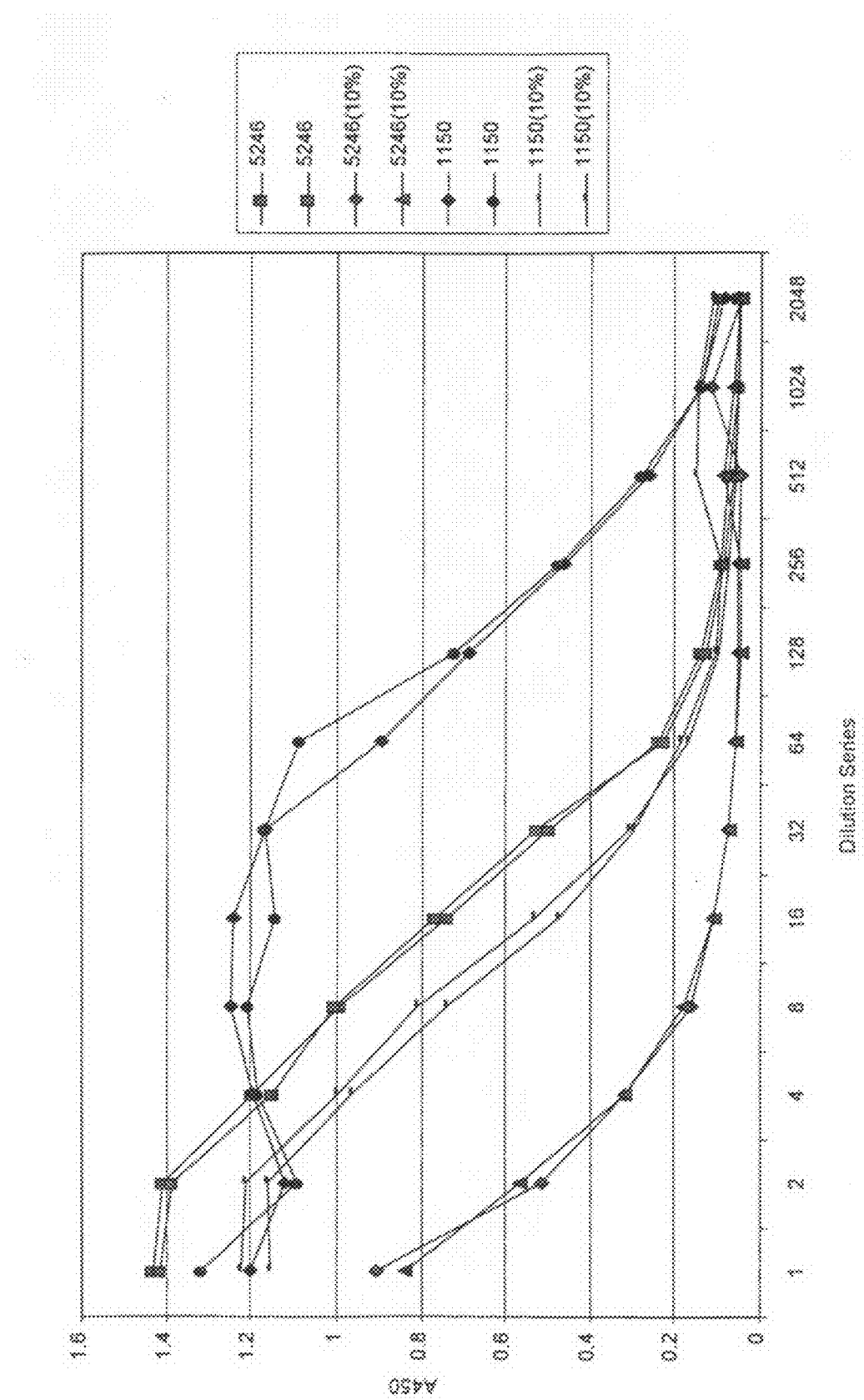
FIG. 4 shows results of an ELISA demonstrating antigen-binding activity of Fab Fragments present in the periplasmic fraction of SE6004 cells. Serial dilutions of periplasmic extracts from cells transformed with plasmid KB5246 or a ten-fold dilution of the extract (5246 10%) are analyzed for binding to PcrV antigen in comparison with a standard periplasmic extract (1150) or a ten-fold dilution (1150 10%) containing anti-PcrV Fab expressed in a wild-type *E. coli* strain with signal peptides to direct secretion. PcrV binding is revealed as an increase in absorbance at 450 nm as a result of enzymatic conversion of TMB substrate to a colored product by HRP-conjugated antibody.

Antigen-binding ELISA confirmed the presence of functional Fab 1A8 in the periplasm (see FIG. 4) and released into the medium of SE6004 transformants containing plasmid KB5246. FIG. 4 demonstrates secretion of significant amounts of Fab fragment capable of binding to PcrV in comparison with a standard preparation of Fab fragment in the periplasm of cells expressing Fab 1A8 in a signal-dependent manner (preparation 1150 in FIG. 4).

Thus the heavy and light chains of Fab 1A8 are secreted from prlA4 mutant E. coli without the need for a signal peptide on either chain. The two chains assemble to form Fab fragment which can be detected in the periplasm and released into the culture medium as functional antigen-binding molecules.

Example 2

Detection of Antigen-Binding Fabs by Colony-Lift Binding Assay (CLBA)

Libraries of antibody Fab fragments cloned in plasmid KB5246 and transformed into SE6004 are plated onto 2YT agar (Becton, Dickinson Difco™ 2×YT yeast extract tryptone medium) containing the appropriate antibiotic (chloramphenicol at 34 µg/ml). The plating efficiency is adjusted so the resulting bacterial colonies are discreet but dense enough to maximize the area of the plate. Various sizes of plate are used depending on the number of clonal colonies to be screened. Thus, at optimal density a 10 cm diameter plate contains 4000 colonies, a 15 cm diameter plate contains 10000 colonies and a 25 cm square plate contains 50,000 colonies.

Nitrocellulose filters (Schleicher & Schuell BA85) of diameter 8.2 cm, 13.2 cm or 20 cm square are pre-coated with antigen in Phosphate Buffered Saline (PBS) at an empirically determined concentration (usually between 0.5 and 20 µg/ml). The volume of coating solution depends upon the filter size. 4 ml, 8 ml or 20 ml can be used for the various filter sizes listed above. Filters are placed face down in a pool of the antigen and capillary action evenly distributes the antigen. The filters are coated for 2-3 hours at 33° C. with occasional agitation. The filters are then rinsed once with excess PBS and blocked with a 5% solution of non-fat dry milk in PBS for an additional 2 hours at 25° C. with agitation. The filters are then drained and rinsed once in PBS supplemented with 0.1% Tween 20 (PBST) and twice in excess 2YT liquid media supplemented with antibiotic selection (34 µg/ml chloramphenicol) and transcriptional inducer (IPTG). The IPTG concentration can be optimized for each library but is typically in the range 0.01-0.1 mM. After allowing the filters to drain, they are placed on a 2YT-agar plate supplemented with the same concentration of antibiotic and inducer (the expression plate).

Un-coated, dry nitrocellulose membrane is placed face-down on the plates of colonies containing the antibody-fragment library. Once the filters are visibly wet (~20 sec) and in one movement, the filters are lifted and placed colony side up onto the coated filter which is already on the expression plate. A sterile needle is used pierce the filters in a pattern which will allow alignment.

The expression plate with the nitrocellulose filter sandwich is placed at 33° C. for 12-16 hours. During this time, the antibody fragments are secreted and diffuse through the first nitrocellulose membrane to the second, antigen-coated membrane. If the antibody fragment from a given bacterial colony has antigen binding activity, it is retained on the antigen filter and is subsequently detected.

After the 12-16 hour expression period, the colony filter is removed from the expression plate and stored at 4° C. on a 2YT-agar plate with antibiotic selection but no transcriptional inducer.

The antigen-coated filter is removed and washed three times (5 minute washes) in excess PBST followed by blocking with a 5% solution of non-fat dry milk in PBST for 1.5 hours at 25° C. The antibody fragments retained on the antigen filter are then detected by first incubating with one of the following alternative primary antibodies: Goat anti-human Kappa-HRP conjugate (US Biological) is used to reveal binding. After four 10-minute washes, the filters are incubated in peroxidase substrate solution (ECL plus, GE Healthcare) and used to expose light-sensitive photographic film. Alternatively, antibodies conjugated with fluorescent labels may be used. In this case a flatbed excitation scanner such as the Typhoon (GE Healthcare), FX-Pro (Biorad) or Odyssey (Li-cor) can be used to visualize the positive spots.

Using a light box for back illumination, the pattern of spots on the photographic film or digital image is aligned with the colony filter (the filter can be removed from the 2YT-agar plate and placed on a plastic transparency for this process). The identified positive colonies are picked and used to inoculate a 2YT liquid mini-culture. Bacteria from the primary screen are then re-plated at a lower density and picked for subsequent analysis to ensure that a clonal population is expanded.

Example 3

Detection of Anti-PcrV Fab Secreted from prlA4 Cells without Signal Peptides Using CLBA For Fab fragments expressed without signal peptides in plasmid KB5246, transformed cells were plated on 2YT expression plates containing chloramphenicol (34 µg/ml) and 10 µM IPTG. Cells were induced for 16 hours and antibody fragments binding to GST-PcrV on the antigen-coated filter were detected as described in Example 2, using a goat anti-human kappa antibody-Horseradish peroxidase conjugate (US Biological) at a dilution of 1/5000 in PBST. After four 15-minute washes and the application of ECL Plus (GE Healthcare), the filters were used to expose autoradiographic film (Hyperfilm from GE Healthcare).

Plasmid KB5246, expressing Fab1A8, was transformed into SE6004 cells, which have a mutant SecY gene (containing the prlA4 mutation), and into TOP10 cells which contain a wild type SecY gene. Positive colonies secreting Fab1A8 were detected in the PcrV antigen-CLBA only from SE6004 transformants; the TOP10 transformants did not secrete detectable amounts of Fab1A8. This result indicates that the prlA4 mutant strain is able to secrete Fab fragment without the need for a signal peptide on either the heavy or light chain. The heavy and light chains assemble and are capable of forming fully functional Fab fragment capable of binding the cognate antigen coated onto a nitrocellulose filter.

Example 4

Screening for Binders to Specific Antigens of Fabs Secreted without Signal Peptides A second human Fab FB42-8, specific for a human cytokine, was expressed without signal peptides in SE6004 by cloning the appropriate V-regions sequences into KB5246 in place of the Fab1A8 V-regions. Cells expressing the two Fabs (FB42-8 and Fab1A8) were mixed in a 50/50 ratio and plated on 2×YT agar. A CLBA was performed as described in Example 2, with the coated antigen being either PCRV or the cytokine antigen specific for FB42-8. Duplicate CLBA, detection and alignment showed that Fabs specific for each antigen could be picked from a mixture of the two transformants.

A library of diverse Fabs can be screened for binders to a specific antigen in the same manner.

Example 5

Efficiency of Secretion of Fabs without Signal Peptides

Figure 5:
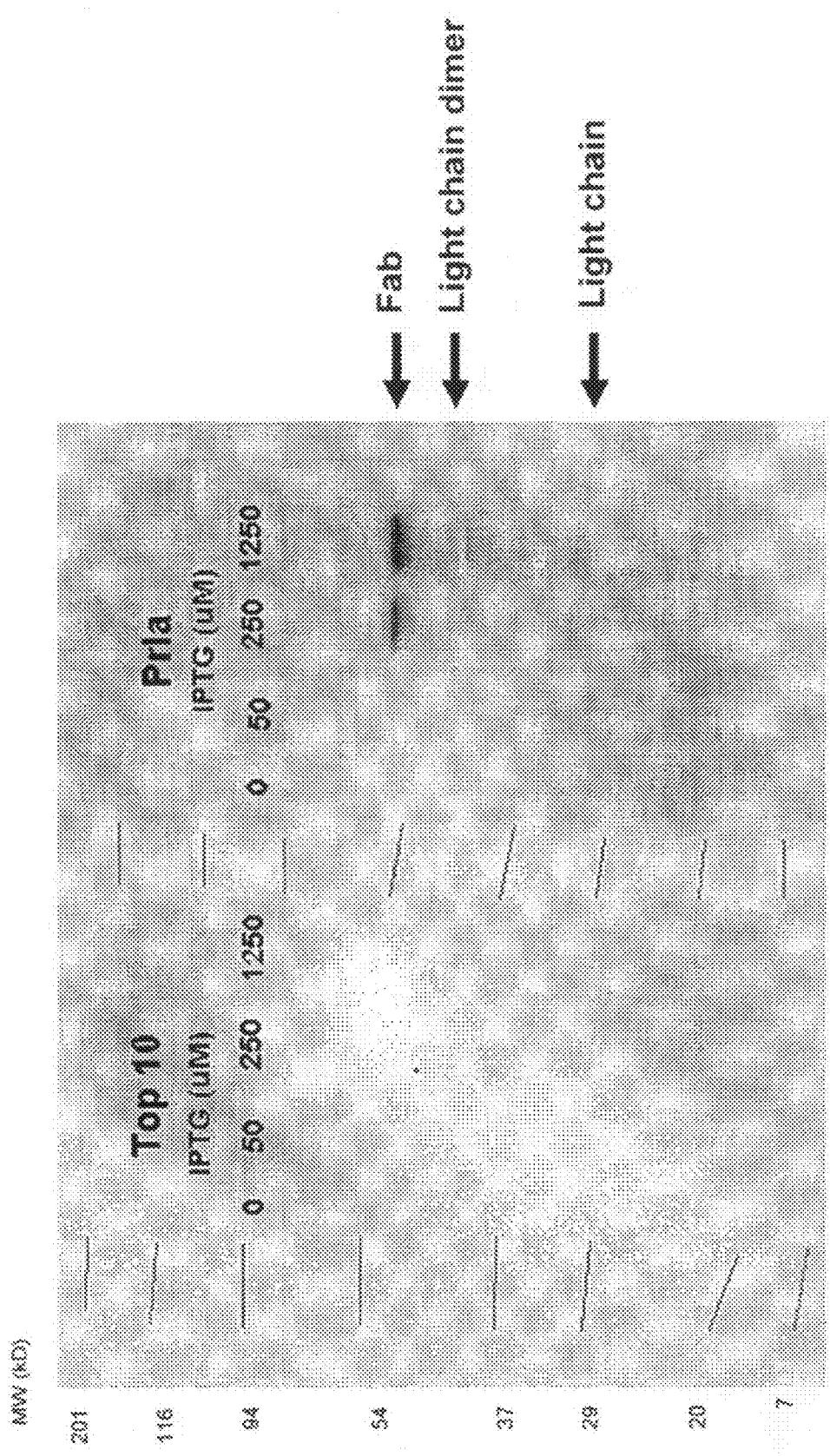
FIG. 5 is a comparison of secretion efficiency for Fab from SE6004 and Top10F' cells identified in periplasmic extracts. Fab was expressed using IPTG (SEQ ED NO:2) induction at the concentrations shown in SE6004 cells (prlA) without the use of signal peptides. Expression is compared with signal-dependent expression of the same Fab from a wild-type strain (TOP10F'). Fab present in periplasmic extracts is detected by Western blot analysis using an anti-human kappa detection reagent.

A Fab was cloned into either a typical bacterial expression plasmid with bacterial secretion leader-peptides (KB1150) or into KB5246 in place of the Fab 1A8 coding sequences. These two constructs were compared for efficiency of expression and secretion at various IPTG induction conditions. Cultures were grown until OD0.6 at 600 nm and then induced. Growth was continued for 16 hrs. Fab secreted into the culture medium was detected on a western blot by an anti-kappa-HRP polyclonal, as in Example 1 (see FIG. 5).

Fabs containing murine V-regions are known to be difficult to express to high yields in bacteria. In this experiment the Fabs secreted more efficiently without signal peptides from SE6004 than when expressed with signal peptides in the wild-type TOP10 strain. Indeed, Fab secretion was undetectable using signal-peptide mediated secretion in TOP10F' cells and was readily detectable in the medium when the SE6004 strain was used for secretion of signal-less Fab. Thus Fabs and other antibodies which are poorly expressed in *E. coli* may advantageously be produced by secretion in the absence of signal peptides from appropriate mutant strains such as the prlA4 mutant SE6004.

Example 6

Construction of an Expression Vector for a prlA4 Mutant secY Gene

An expression vector, p15A, for expression of genes in bacterial cells under the control of a strong bacterial promoter, the trc promoter, was constructed as follows.

Plasmid pACYC177 (Fermentas) was digested with BanI and partially digested with StuI. The 2386 by DNA fragment was then blunt-ended using Klenow fragment of DNA polymerase I. The pTrc promoter was PCR amplified from the plasmid p6xHis-GFP (Clontech) with the following primers:

```
Primer 1:                             (SEQ ID NO: 12)
TCTTCCAGGCCTGAGCTCGAGCTGTTGACAATTAATCA Primer 2:                             (SEQ ID NO: 13)
CAGTTACAGGCCTGGTACCTCACCGGCCGTTAAACCCCCCAT

GGTTTATTCC
```

The PCR product was then digested with StuI, and ligated with the 2386 DNA fragment of pACYC177 to give vector p15A, which has NcoI and KpnI sites after the pTrc promoter.

The prlA4 mutant SecY gene was cloned from SE6004 cells by PCR amplification using the following primers:

```
Primer3:                                     (SEQ ID NO: 14)
ACGGAATTCACCATGGCTAAACAACCGGGATTAGATTTTC Primer4:                                     (SEQ ID NO: 15)
CAGTTACGGTACCTTATCGGCCGTAGCCTTTCAGGTTC
```

Figure 6:
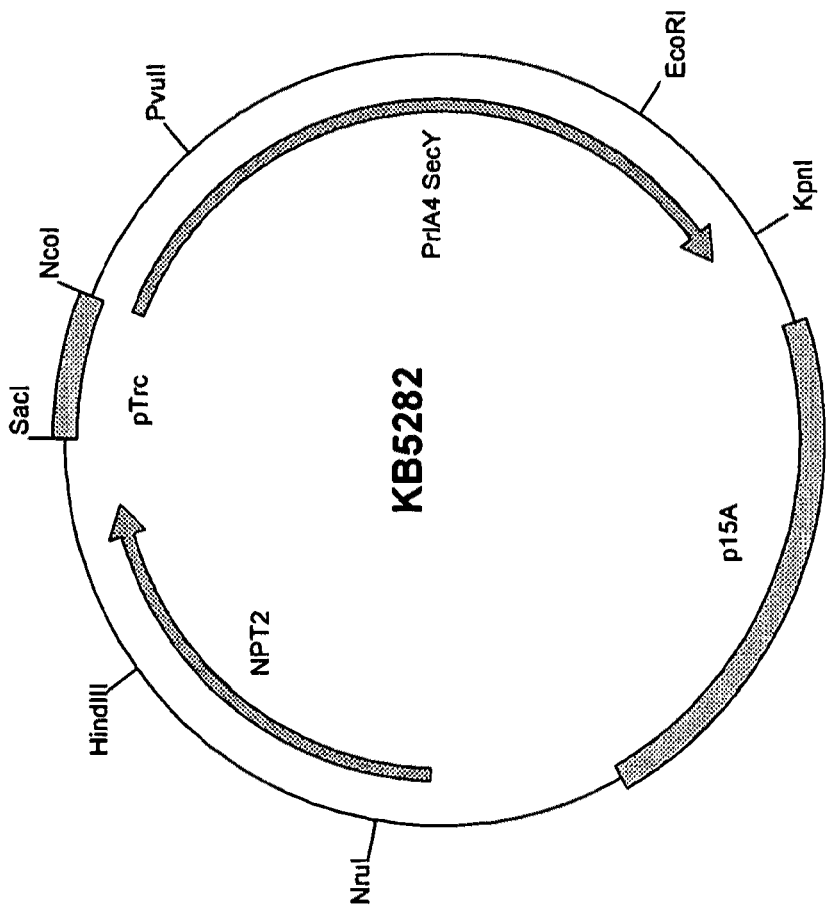
FIG. 6 is a Map of plasmid KB5282 for the over-expression of mutant SecY. The prlA4 mutant SecY gene is expressed from the pTrc promoter. The NPT2 gene confers resistance to kanamycin.

The PCR product was then digested with NcoI and KpnI and cloned into vector p15A between the same two sites to give KB5282 which expresses the mutant SecY gene under the control of the bacterial trc promoter (pTrc; see FIG. 6). Transformation of E. coli strains with KB5282 confers the prlA phenotype on the host cell and allows secretion via the periplasm of heterologous proteins such as antibodies from coding sequences which do not encode signal peptides.

Electro-competent DH5-alpha cells were transformed with plasmid KB5282 by electroporation and transformants were selected using 35 µg/ml kanamycin in 2×YT medium.

Figure 7:
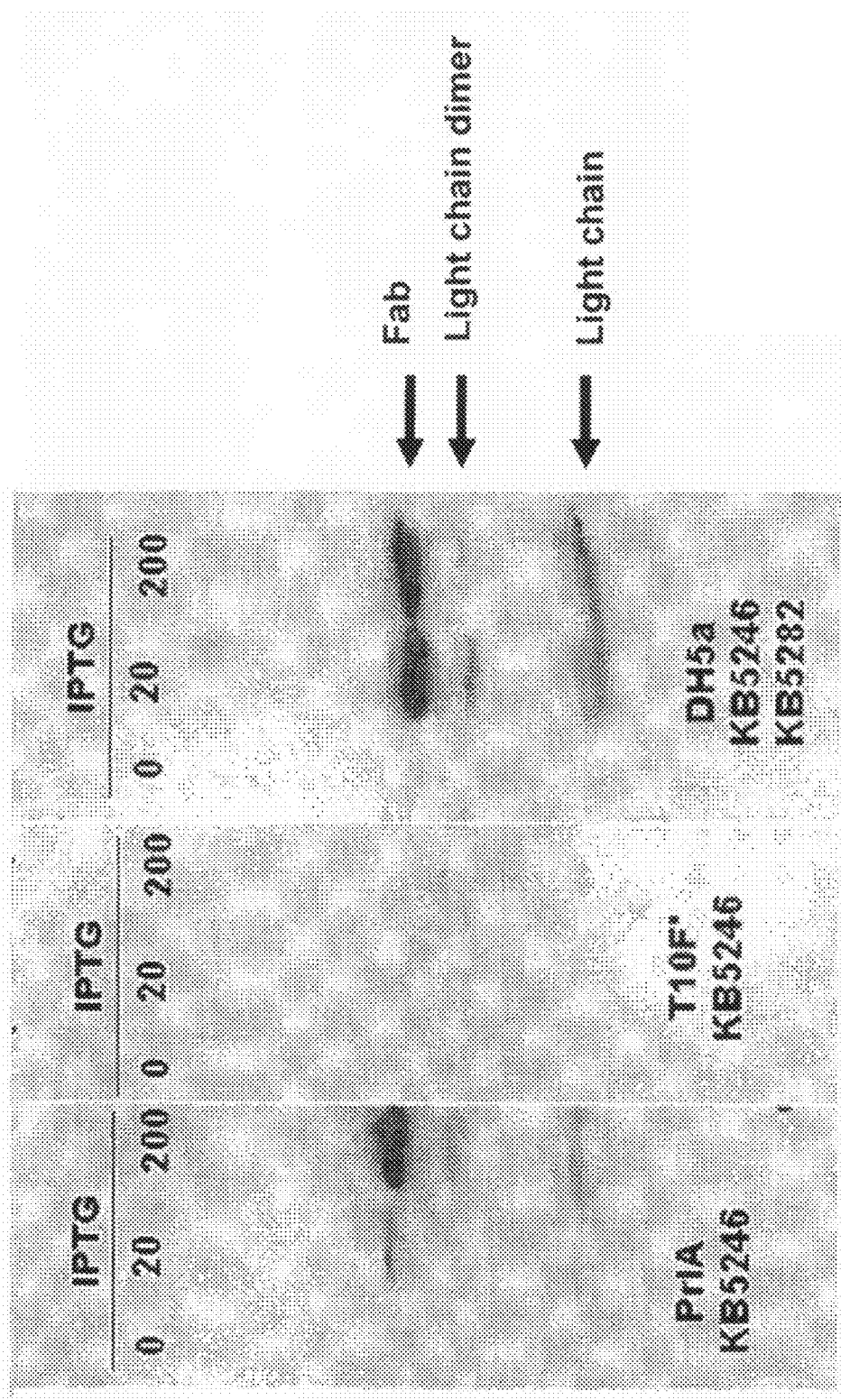
FIG. 7 is a Western blot analysis comparing the secretion efficiency for Fab 1A8 from the prlA4 mutant strain SE6004, Top10F' cells expressing wild-type SecY, and DH5α cells co-transformed with a prlA4 mutant SecY gene. Antibody-related proteins secreted into the medium were detected using anti-human kappa antibody of blots from non-denaturing SDS-PAGE. Assembled Fab, light-chain dimers and light chain monomers were detected in the culture medium.

The expression of Fab1A8 in DH5α cells in the presence of overexpressed mutant SecY was assessed as follows. DH5α cells were co-transformed by electroporation with plasmids KB5246 (expressing the Fab without signal sequences) and KB5282 (expressing mutant SecY). Transformants selected on chloramphenicol and Kanamycin were cultured in 2×YT medium and expression of the heavy and light chains of Fab1A8 was induced using isopropyl-beta-D-thiogalactopyranoside (IPTG) at a concentration of 20 µM or 200 µM. Expression was continued for 16 hours at 33° C. with shaking. The levels of expressed and secreted intact Fab fragments from DH5α cells with the co-transformation of mutant SecY was compared with expression of Fab from the prlA4 strain SE6004 using the same concentrations of IPTG, as described in Example 1. Western blots using a detection antibody specific for human Kappa chains were carried out on expression media run on SDS-PAGE under non-reducing conditions (FIG. 7). High levels of secreted Fab were detected in the media of DH5α cells expressing mutant SecY. Indeed these cells secreted higher levels of Fab when induced using 20 µM IPTG than SE6004 cells. In contrast, no detectable secretion of Fab was observed when KB5246 was transformed into TOP10F' cells, a strain which expresses wild-type SecY, (see FIG. 7).

Example 7

Expression of Antibody Fragments with Signal Sequences in prl Mutant E. coli Strains Expression vectors which encode antibody polypeptides including signal peptides can also be expressed in a prl mutant E. coli strain as follows. A signal peptide is introduced at the N-terminus of the heavy chain coding sequence, the light chain coding sequence or both in order to secrete assembled and functional Fab or Fab' fragments from the prl mutant strain.

To generate a convenient prl mutant strain for the expression of antibody fragments containing signal peptides, plasmid KB5282 (Example 6) is used to transform DH5-alpha cells. The kanamycin-resistant transformants have the prlA phenotype and can secrete Fab fragments lacking signal peptides as described in Example 6. In this case the KB5282 DH5-alpha transformants are subsequently transformed by electroporation with an expression vector expressing antibody heavy and light chains in which one or both of the chains is expressed with a signal peptide. Electrocompetent cells are prepared according to standard techniques as described in Short Protocols in *Molecular Biology* (3rd edition), Ausubel et al (John Wiley and Sons Inc.) and electroporation is carried out as described in Example 1.

Functional Fab or Fab' fragments are identified and may be isolated from the periplasmic fraction or the culture medium as described in Examples 1, 2 and 3 above.

---

What is claimed is:

1. A method for producing an antibody, comprising the steps of:
    (a) culturing an *E. coli* host cell comprising a prlA4 (SEQ ID NO: 1) phenotype and at least one expression vector comprising a polynucleotide molecule encoding a heavy chain polypeptide of the antibody and a polynucleotide molecule encoding a light chain polypeptide of the antibody, under conditions that express the polynucleotide encoding the heavy chain polypeptide and the polynucleotide molecule encoding the light chain polypeptide of the antibody, wherein at least one of the polynucleotides encodes a polypeptide lacking a signal peptide,
    (b) secreting the heavy chain polypeptide and the light chain polypeptide across a cytoplasmic membrane,
    (c) forming the antibody from the heavy chain polypeptide and the light chain polypeptide, and
    (d) isolating said antibody.

2. The method of claim 1, wherein the antibody is selected from the group consisting of a human antibody, a mouse antibody, a rat antibody, a rabbit antibody, a camel antibody, a sheep antibody, a chimeric antibody, a humanized antibody, a fusion antibody, and an epitope-focused antibody.

3. The method of claim 1, wherein the polynucleotides encoding the heavy chain polypeptide and the light chain polypeptide are present on different expression vectors.

4. The method of claim 1, wherein the polynucleotides encoding the heavy chain polypeptide and the light chain polypeptide are both present on the same vector.

5. The method of claim 1, wherein the polynucleotide encodes the heavy chain polypeptide lacking a signal peptide.

6. The method of claim 1, wherein the polynucleotide encodes the light chain polypeptide lacking a signal peptide.

7. The method of claim 1, wherein the polynucleotides encode the heavy and light chain polypeptides lacking signal peptides.

* * * * *